United States Patent
Kalafut et al.

(10) Patent No.: US 11,191,501 B2
(45) Date of Patent: *Dec. 7, 2021

(54) SYSTEMS AND METHODS FOR DETERMINATION OF PHARMACEUTICAL FLUID INJECTION PROTOCOLS BASED ON X-RAY TUBE VOLTAGE

(71) Applicant: Bayer HealthCare LLC, Whippany, NJ (US)

(72) Inventors: John F. Kalafut, Pittsburgh, PA (US); Corey A. Kemper, Pittsburgh, PA (US)

(73) Assignee: BAYER HEALTHCARE LLC, Whippany, NJ (US)

(*) Notice: Subject to any disclaimer, the term of this patent is extended or adjusted under 35 U.S.C. 154(b) by 802 days.

This patent is subject to a terminal disclaimer.

(21) Appl. No.: 15/959,695

(22) Filed: Apr. 23, 2018

(65) Prior Publication Data
US 2018/0242940 A1 Aug. 30, 2018

Related U.S. Application Data

(63) Continuation of application No. 14/401,330, filed as application No. PCT/US2012/037744 on May 14, 2012, now Pat. No. 9,949,704.

(51) Int. Cl.
*A61B 6/00* (2006.01)
*A61B 6/03* (2006.01)

(52) U.S. Cl.
CPC .......... *A61B 6/481* (2013.01); *A61B 6/00* (2013.01); *A61B 6/032* (2013.01); *A61B 6/469* (2013.01);
(Continued)

(58) Field of Classification Search
CPC ......... A61B 6/481; A61B 6/469; A61B 6/482; A61B 6/504; A61B 6/545; A61B 6/032; A61B 6/54; A61B 6/00
See application file for complete search history.

(56) References Cited

U.S. PATENT DOCUMENTS 3,349,713 A 10/1967 Fassbender
3,520,295 A 7/1970 Paul
(Continued)

FOREIGN PATENT DOCUMENTS

AT 259621 T 3/2004
AU 7381796 A 4/1997
(Continued)

OTHER PUBLICATIONS

Van Der Wall, E.E., et al., 100 kV versus 120 kV: effective reduction in radiation dose?, Int J Cardiovasc Imaging, 2011, pp. 587-591, vol. 27.
(Continued)

*Primary Examiner* — Bo Joseph Peng
(74) *Attorney, Agent, or Firm* — James R. Stevenson; Bryan Clark

(57) ABSTRACT

A system for patient imaging is provided. The system includes an imaging system and a parameter generator to determine parameters of at least a first phase of an injection procedure. The imaging system includes a scanner that has at least one x-ray tube. The parameter generator is programmed to determine at least one of the parameters on the basis of a voltage to be applied to the at least one x-ray tube during an imaging procedure. A method of controlling an injector system is also provided, and the method includes determining injection parameters, at least one of which is determined on the basis of a voltage to be applied to an x-ray tube during the imaging procedure, as well as controlling the injector system at least in part on the basis of the determined injection parameters.

28 Claims, 27 Drawing Sheets

(52) U.S. Cl.
CPC .............. *A61B 6/482* (2013.01); *A61B 6/504* (2013.01); *A61B 6/54* (2013.01); *A61B 6/545* (2013.01)

(56) References Cited

U.S. PATENT DOCUMENTS

| | | |
|---|---|---|
| 3,523,523 A | 8/1970 | Heinrich et al. |
| 3,623,474 A | 11/1971 | Heilman |
| 3,701,345 A | 10/1972 | Heilman |
| 3,755,655 A | 8/1973 | Senecal |
| 3,793,600 A | 2/1974 | Grosbard |
| 3,812,843 A | 5/1974 | Wootten et al. |
| 3,817,843 A | 6/1974 | Barrett |
| 3,839,708 A | 10/1974 | Lyons et al. |
| 3,888,239 A | 6/1975 | Rubinstein |
| 3,895,220 A | 7/1975 | Nelson et al. |
| 3,898,983 A | 8/1975 | Elam |
| 3,927,955 A | 12/1975 | Spinosa et al. |
| 3,941,126 A | 3/1976 | Dietrich et al. |
| 3,958,103 A | 5/1976 | Oka et al. |
| 3,968,195 A | 7/1976 | Bishop |
| 3,995,381 A | 12/1976 | Manfred et al. |
| 4,001,549 A | 1/1977 | Corwin |
| 4,006,736 A | 2/1977 | Kranys et al. |
| 4,038,981 A | 8/1977 | Lefevre et al. |
| 4,044,757 A | 8/1977 | McWhorter et al. |
| 4,090,502 A | 5/1978 | Tajika |
| 4,135,247 A | 1/1979 | Gordon et al. |
| 4,151,845 A | 5/1979 | Clemens |
| 4,187,057 A | 2/1980 | Xanthopoulos |
| 4,191,183 A | 3/1980 | Mendelson |
| 4,199,000 A | 4/1980 | Edstrom |
| 4,207,871 A | 6/1980 | Jenkins |
| 4,223,675 A | 9/1980 | Williams |
| 4,262,824 A | 4/1981 | Hrynewycz |
| 4,263,916 A | 4/1981 | Brooks et al. |
| 4,280,494 A | 7/1981 | Cosgrove, Jr. et al. |
| 4,284,073 A | 8/1981 | Krause et al. |
| 4,315,247 A | 2/1982 | Germanton |
| 4,319,568 A | 3/1982 | Tregoning |
| 4,340,153 A | 7/1982 | Spivey |
| 4,341,153 A | 7/1982 | Bowser |
| 4,392,847 A | 7/1983 | Whitney et al. |
| 4,392,849 A | 7/1983 | Petre et al. |
| 4,396,385 A | 8/1983 | Kelly et al. |
| 4,402,310 A | 9/1983 | Kimura |
| 4,409,966 A | 10/1983 | Lambrecht et al. |
| 4,434,820 A | 3/1984 | Glass |
| 4,434,822 A | 3/1984 | Bellamy et al. |
| 4,435,173 A | 3/1984 | Siposs et al. |
| 4,444,198 A | 4/1984 | Petre |
| 4,447,230 A | 5/1984 | Gula et al. |
| 4,448,200 A | 5/1984 | Brooks et al. |
| 4,474,476 A | 10/1984 | Thomsen |
| 4,477,923 A * | 10/1984 | Baumann ............... A61B 6/481 378/95 |
| 4,479,760 A | 10/1984 | Bilstad et al. |
| 4,479,761 A | 10/1984 | Bilstad et al. |
| 4,479,762 A | 10/1984 | Bilstad et al. |
| 4,504,908 A | 3/1985 | Riederer et al. |
| 4,509,526 A | 4/1985 | Barnes et al. |
| 4,512,764 A | 4/1985 | Wunsch |
| 4,542,459 A | 9/1985 | Riederer |
| 4,544,949 A | 10/1985 | Kurihara |
| 4,551,133 A | 11/1985 | Zegers De Beyl et al. |
| 4,552,130 A | 11/1985 | Kinoshita |
| 4,559,036 A | 12/1985 | Wunsch |
| 4,563,175 A | 1/1986 | Lafond |
| 4,578,802 A | 3/1986 | Itoh |
| 4,585,009 A | 4/1986 | Barker et al. |
| 4,585,941 A | 4/1986 | Bergner |
| 4,610,670 A | 9/1986 | Spencer |
| 4,610,790 A | 9/1986 | Reti et al. |
| 4,611,340 A | 9/1986 | Okazaki |
| 4,612,572 A | 9/1986 | Komatsu et al. |
| 4,625,494 A | 12/1986 | Iwatschenko et al. |
| 4,626,144 A | 12/1986 | Berner |
| 4,633,307 A | 12/1986 | Honda |
| 4,634,426 A | 1/1987 | Kamen |
| 4,636,144 A | 1/1987 | Abe et al. |
| 4,655,197 A | 4/1987 | Atkinson |
| 4,662,906 A | 5/1987 | Matkovich et al. |
| 4,672,651 A | 6/1987 | Horiba et al. |
| 4,676,776 A | 6/1987 | Howson |
| 4,682,170 A | 7/1987 | Kubota et al. |
| 4,689,670 A | 8/1987 | Okazaki |
| 4,710,166 A | 12/1987 | Thompson et al. |
| 4,723,261 A | 2/1988 | Janssen et al. |
| 4,750,643 A | 6/1988 | Wortrich |
| 4,754,786 A | 7/1988 | Roberts |
| 4,781,687 A | 11/1988 | Wall |
| 4,783,273 A | 11/1988 | Knutsson et al. |
| 4,789,014 A | 12/1988 | Digianfilippo et al. |
| 4,793,357 A | 12/1988 | Lindstrom |
| 4,795,429 A | 1/1989 | Feldstein |
| 4,798,590 A | 1/1989 | O'Leary et al. |
| 4,804,454 A | 2/1989 | Asakura et al. |
| 4,823,833 A | 4/1989 | Hogan et al. |
| 4,835,521 A | 5/1989 | Andrejasich et al. |
| 4,836,187 A | 6/1989 | Iwakoshi et al. |
| 4,838,856 A | 6/1989 | Mulreany et al. |
| 4,840,620 A | 6/1989 | Kobayashi et al. |
| 4,844,052 A | 7/1989 | Iwakoshi et al. |
| 4,853,521 A | 8/1989 | Claeys et al. |
| 4,854,301 A | 8/1989 | Nakajima |
| 4,854,324 A | 8/1989 | Hirschman et al. |
| 4,857,056 A | 8/1989 | Talonn |
| 4,874,359 A | 10/1989 | White et al. |
| 4,879,880 A | 11/1989 | Harrison |
| 4,880,014 A | 11/1989 | Zarowitz et al. |
| 4,887,208 A | 12/1989 | Schneider et al. |
| 4,887,554 A | 12/1989 | Whitford |
| 4,901,731 A | 2/1990 | Millar |
| 4,903,705 A | 2/1990 | Imamura et al. |
| 4,913,154 A | 4/1990 | Ermert et al. |
| 4,922,916 A | 5/1990 | Ermert et al. |
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |

(56) References Cited

U.S. PATENT DOCUMENTS

| | | |
|---|---|---|
| 5,108,365 A | 4/1992 | Woods, Jr. |
| 5,111,492 A | 5/1992 | Klausz |
| 5,113,904 A | 5/1992 | Aslanian |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,150,292 A | 9/1992 | Hoffmann et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | MacVicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,174 A | 1/1994 | Plotkin et al. |
| 5,276,614 A | 1/1994 | Heuscher |
| 5,286,252 A | 2/1994 | Tuttle et al. |
| 5,287,273 A | 2/1994 | Kupfer et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | McKee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,058 A | 1/1995 | Yonezawa |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,417,219 A | 5/1995 | Takamizawa et al. |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,681,285 A | 10/1997 | Ford et al. |
| 5,687,208 A | 11/1997 | Bae et al. |
| 5,687,708 A | 11/1997 | Farnsworth et al. |
| 5,713,358 A | 2/1998 | Mistretta et al. |
| 5,724,976 A | 3/1998 | Mine et al. |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,881,124 A | 3/1999 | Giger et al. |
| 5,882,343 A | 3/1999 | Wilson et al. |
| 5,885,216 A | 3/1999 | Evans, III et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,149,627 A | 11/2000 | Uber, III |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,337,992 B1 | 1/2002 | Gelman |
| 6,344,030 B1 | 2/2002 | Duchon et al. |

(56) References Cited

U.S. PATENT DOCUMENTS

| | | |
|---|---|---|
| 6,346,229 B1 | 2/2002 | Driehuys et al. |
| 6,381,486 B1 | 4/2002 | Mistretta et al. |
| 6,385,483 B1 | 5/2002 | Uber, III et al. |
| 6,387,098 B1 | 5/2002 | Cole et al. |
| 6,397,093 B1 | 5/2002 | Aldrich |
| 6,397,097 B1 | 5/2002 | Requardt |
| 6,397,098 B1 | 5/2002 | Uber, III et al. |
| 6,402,697 B1 | 6/2002 | Calkins et al. |
| 6,423,719 B1 | 7/2002 | Lawyer |
| 6,442,418 B1 | 8/2002 | Evans, III et al. |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zaiezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,866,654 B2 | 3/2005 | Callan et al. |
| 6,876,720 B2 | 4/2005 | Tsuyuki |
| 6,879,853 B2 | 4/2005 | Meaney et al. |
| 6,887,214 B1 | 5/2005 | Levin et al. |
| 6,889,074 B2 | 5/2005 | Uber et al. |
| 6,898,453 B2 | 5/2005 | Lee |
| 6,901,283 B2 | 5/2005 | Evans et al. |
| 6,970,735 B2 | 11/2005 | Uber et al. |
| 6,972,001 B2 | 12/2005 | Emig et al. |
| 6,983,590 B2 | 1/2006 | Roelle et al. |
| 6,994,700 B2 | 2/2006 | Elkins et al. |
| 7,094,216 B2 | 8/2006 | Trombley et al. |
| 7,104,981 B2 | 9/2006 | Elkins et al. |
| 7,108,981 B2 | 9/2006 | Aoki et al. |
| 7,163,520 B2 | 1/2007 | Bernard et al. |
| 7,266,227 B2 | 9/2007 | Pedain et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,313,431 B2 | 12/2007 | Uber et al. |
| 7,325,330 B2 | 2/2008 | Kim et al. |
| 7,326,186 B2 | 2/2008 | Trombley et al. |
| 7,363,072 B2 | 4/2008 | Movahed |
| 7,492,947 B2 | 2/2009 | Nanbu |
| 7,522,744 B2 | 4/2009 | Bai et al. |
| 7,672,710 B2 | 3/2010 | Uber, III |
| 7,672,711 B2 | 3/2010 | Haras et al. |
| 7,713,239 B2 | 5/2010 | Uber et al. |
| 7,783,091 B2 | 8/2010 | Rinck et al. |
| 7,864,997 B2 | 1/2011 | Aben et al. |
| 7,925,330 B2 | 4/2011 | Kalafut et al. |
| 7,937,134 B2 | 5/2011 | Uber, III |
| 7,996,381 B2 | 8/2011 | Uber, III et al. |
| 8,011,401 B1 | 9/2011 | Utterback |
| 8,055,328 B2 | 11/2011 | Uber, III et al. |
| 8,086,001 B2 | 12/2011 | Bredno et al. |
| 8,160,679 B2 | 4/2012 | Uber, III et al. |
| 8,197,437 B2 | 6/2012 | Kalafut et al. |
| 8,295,914 B2 | 10/2012 | Kalafut et al. |
| 8,315,449 B2 | 11/2012 | Kemper et al. |
| 8,346,342 B2 | 1/2013 | Kalafut et al. |
| 8,428,694 B2 | 4/2013 | Kalafut et al. |
| 8,486,017 B2 | 7/2013 | Masuda et al. |
| 8,705,819 B2 | 4/2014 | Carlsen et al. |
| 8,718,747 B2 | 5/2014 | Bjornerud et al. |
| 9,271,656 B2 | 3/2016 | Korporaal |
| 9,302,044 B2 | 4/2016 | Kalafut et al. |
| 9,421,330 B2 | 8/2016 | Kalafut et al. |
| 2001/0027265 A1 | 10/2001 | Prince |
| 2001/0041964 A1 | 11/2001 | Grass et al. |
| 2002/0010551 A1 | 1/2002 | Wang et al. |
| 2002/0026148 A1 | 2/2002 | Uber et al. |
| 2002/0123702 A1 | 9/2002 | Cho |
| 2002/0151854 A1 | 10/2002 | Duchon et al. |
| 2003/0015078 A1 | 1/2003 | Taylor |
| 2003/0050556 A1 | 3/2003 | Uber et al. |
| 2003/0120171 A1 | 6/2003 | Diamantopoulos et al. |
| 2003/0195462 A1 | 10/2003 | Mann et al. |
| 2003/0198691 A1 | 10/2003 | Cheung et al. |
| 2003/0212364 A1 | 11/2003 | Mann et al. |
| 2003/0216683 A1 | 11/2003 | Shekalim |
| 2004/0011740 A1 | 1/2004 | Bernard et al. |
| 2004/0025452 A1 | 2/2004 | McLean |
| 2004/0039530 A1 | 2/2004 | Leesman et al. |
| 2004/0064041 A1 | 4/2004 | Lazzaro et al. |
| 2004/0097806 A1 | 5/2004 | Hunter et al. |
| 2004/0162484 A1 | 8/2004 | Nemoto |
| 2004/0163655 A1 | 8/2004 | Gelfand et al. |
| 2004/0167415 A1 | 8/2004 | Gelfand et al. |
| 2004/0215144 A1 | 10/2004 | Duchon et al. |
| 2004/0242994 A1 | 12/2004 | Brady et al. |
| 2005/0004517 A1 | 1/2005 | Courtney et al. |
| 2005/0053551 A1 | 3/2005 | Badiola |
| 2005/0112178 A1 | 5/2005 | Stern |
| 2005/0256441 A1 | 11/2005 | Lotan et al. |
| 2006/0013772 A1 | 1/2006 | Lewinter et al. |
| 2006/0052764 A1 | 3/2006 | Gelfand et al. |
| 2006/0074294 A1 | 4/2006 | Williams, Jr. et al. |
| 2006/0079843 A1 | 4/2006 | Brooks et al. |
| 2006/0096388 A1 | 5/2006 | Gysling et al. |
| 2006/0184099 A1 | 8/2006 | Hong |
| 2006/0211989 A1 | 9/2006 | Rhinehart et al. |
| 2006/0235353 A1 | 10/2006 | Gelfand et al. |
| 2006/0235474 A1 | 10/2006 | Demarais |
| 2006/0239918 A1 | 10/2006 | Klotz et al. |
| 2006/0253064 A1 | 11/2006 | Gelfand et al. |
| 2006/0253353 A1 | 11/2006 | Weisberger |
| 2006/0270971 A1 | 11/2006 | Gelfand et al. |
| 2006/0271111 A1 | 11/2006 | Demarais et al. |
| 2007/0016016 A1 | 1/2007 | Haras et al. |
| 2007/0078330 A1 | 4/2007 | Haras et al. |
| 2007/0213662 A1 | 9/2007 | Kalafut et al. |
| 2007/0225601 A1 | 9/2007 | Uber, III |
| 2007/0244389 A1 | 10/2007 | Hoppel et al. |
| 2007/0282199 A1 | 12/2007 | Uber, III |
| 2008/0009717 A1 | 1/2008 | Herrmann et al. |
| 2008/0045834 A1 | 2/2008 | Uber, III |
| 2008/0046286 A1 | 2/2008 | Halsted |
| 2008/0097339 A1 | 4/2008 | Ranchod et al. |
| 2008/0101678 A1 | 5/2008 | Suliga et al. |
| 2008/0119715 A1 | 5/2008 | Gonzalez et al. |
| 2008/0294035 A1 | 11/2008 | Zwick et al. |
| 2009/0028968 A1 | 1/2009 | Tam et al. |
| 2009/0116711 A1 | 5/2009 | Larson et al. |
| 2009/0177050 A1 | 7/2009 | Griffiths et al. |
| 2009/0226867 A1 | 9/2009 | Kalafut et al. |
| 2010/0030073 A1 | 2/2010 | Kalafut |
| 2010/0113887 A1* | 5/2010 | Kalafut ............... A61M 5/007 |
| | | 600/300 |
| 2011/0200165 A1 | 8/2011 | Pietsch |
| 2012/0016233 A1 | 1/2012 | Kalafut et al. |
| 2012/0141005 A1 | 6/2012 | Djeridane et al. |
| 2013/0041257 A1 | 2/2013 | Nemoto |

(56) References Cited

U.S. PATENT DOCUMENTS

| | | |
|---|---|---|
| 2013/0044926 A1 | 2/2013 | Kemper et al. |
| 2013/0211247 A1 | 8/2013 | Kalafut et al. |

FOREIGN PATENT DOCUMENTS

| | | |
|---|---|---|
| CA | 2045070 A1 | 2/1992 |
| CA | 2077712 A1 | 12/1993 |
| CA | 2234050 A1 | 4/1997 |
| DE | 3203594 A1 | 8/1983 |
| DE | 3726452 A1 | 2/1989 |
| DE | 4121568 A1 | 10/1992 |
| DE | 4426387 A1 | 8/1995 |
| DE | 19702896 A1 | 7/1997 |
| DE | 69631607 T2 | 12/2004 |
| DK | 0869738 T3 | 6/2004 |
| EP | 0121216 A1 | 10/1984 |
| EP | 0129910 A1 | 1/1985 |
| EP | 0189491 A1 | 8/1986 |
| EP | 0192786 A2 | 9/1986 |
| EP | 0245160 A1 | 11/1987 |
| EP | 0319275 A1 | 6/1989 |
| EP | 0337924 A2 | 10/1989 |
| EP | 0343501 A2 | 11/1989 |
| EP | 0364966 A1 | 4/1990 |
| EP | 0365301 A1 | 4/1990 |
| EP | 0372152 A1 | 6/1990 |
| EP | 0378896 A2 | 7/1990 |
| EP | 0429191 A2 | 5/1991 |
| EP | 0439711 A2 | 8/1991 |
| EP | 0471455 A2 | 2/1992 |
| EP | 0475563 A1 | 3/1992 |
| EP | 0595474 A2 | 5/1994 |
| EP | 0600448 A2 | 6/1994 |
| EP | 0619122 A1 | 10/1994 |
| EP | 0869738 A1 | 10/1998 |
| EP | 2042100 A2 | 4/2009 |
| ES | 2216068 T3 | 10/2004 |
| FR | 2493708 A1 | 5/1982 |
| FR | 2561949 A1 | 10/1985 |
| GB | 201800 A | 8/1923 |
| GB | 2207749 A | 2/1989 |
| GB | 2252656 A | 8/1992 |
| GB | 2328745 A | 3/1999 |
| JP | S5017781 A | 2/1975 |
| JP | S5815842 A | 1/1983 |
| JP | S59214432 A | 12/1984 |
| JP | S60194934 A | 10/1985 |
| JP | S60194935 A | 10/1985 |
| JP | S60253197 A | 12/1985 |
| JP | S62216199 A | 9/1987 |
| JP | S6340538 A | 2/1988 |
| JP | S63290547 A | 11/1988 |
| JP | H01207038 A | 8/1989 |
| JP | H02224647 A | 9/1990 |
| JP | H02234747 A | 9/1990 |
| JP | H0355040 A | 3/1991 |
| JP | H04115677 A | 4/1992 |
| JP | H0584296 A | 4/1993 |
| JP | H07178169 A | 7/1995 |
| JP | H10211198 A | 8/1998 |
| JP | 2000175900 A | 6/2000 |
| JP | 2003102724 A | 4/2003 |
| JP | 2003116843 A | 4/2003 |
| JP | 2003210456 A | 7/2003 |
| JP | 2003225234 A | 8/2003 |
| JP | 2004174008 A | 6/2004 |
| JP | 2004194721 A | 7/2004 |
| JP | 2004236849 A | 8/2004 |
| JP | 2004298550 A | 10/2004 |
| JP | 2006075600 A | 3/2006 |
| JP | 2007020829 A | 2/2007 |
| JP | 2007143880 A | 6/2007 |
| JP | 2007283103 A | 11/2007 |
| WO | 8001754 A1 | 9/1980 |
| WO | 8500292 A1 | 1/1985 |
| WO | 8803815 A1 | 6/1988 |
| WO | 9114232 A1 | 9/1991 |
| WO | 9114233 A1 | 9/1991 |
| WO | 9315658 A1 | 8/1993 |
| WO | 9325141 A1 | 12/1993 |
| WO | 9415664 A1 | 7/1994 |
| WO | 9632975 A1 | 10/1996 |
| WO | 9712550 A1 | 4/1997 |
| WO | 9820919 A1 | 5/1998 |
| WO | 9924095 A2 | 5/1999 |
| WO | 0061216 A1 | 10/2000 |
| WO | 02086821 A1 | 10/2002 |
| WO | 03015633 A1 | 2/2003 |
| WO | 03046795 A2 | 6/2003 |
| WO | 2004012787 A2 | 2/2004 |
| WO | 2005004038 A1 | 1/2005 |
| WO | 2005016165 A1 | 2/2005 |
| WO | 2006042093 A1 | 4/2006 |
| WO | 2007143682 A2 | 12/2007 |
| WO | 2008060629 A2 | 5/2008 |
| WO | 2010115165 A2 | 10/2010 |
| WO | 2011136218 A1 | 11/2011 |
| WO | 2011162578 A2 | 12/2011 |

OTHER PUBLICATIONS

Van Der Wall, E.E., et al., Reduction of radiation dose using 80 kV tube voltage: a feasible strategy?, Int JCardiovasc Imaging, 2011.

Waaijer, Annet, et al., Circle of Willis at CT Angiography: Dose Reduction and Image Quality—Reducing TubeVoltage and Increasing Tube Current Settings, Radiology, Mar. 2007, pp. 832-839, vol. 242, No. 3.

Wada, D.R. and Ward, D.S., "Open loop control of multiple drug effects in anesthesia", IEEE Transactions on Biomedical Engineering, vol. 42, Issue 7, pp. 666-677, 1995.

Wada D.R. and Ward, D.S., "The hybrid model: a new pharmacokinetic model for computer-controlled infusion pumps", IEEE Transactions on Biomedical Engineering, 1994, vol. 41, Issue 2, pp. 134-142.

Wang, Dan, et al., Image quality and dose performance of 80 kV low dose scan protocol in high-pitch spiralcoronary CT angiography: feasibility study, Int J Cardiovasc Imaging, 2011.

Wintersperger, B., et al., Aorto-iliac multidetector-row CT angiography with low kV settings: improved vesselenhancement and simultaneous reduction of radiation dose, Eur Radiol, 2005, pp. 334-341, vol. 15.

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.

"Extended European Search Report from EP Application No. 18170245", dated Jul. 25, 2018.

European Search Report and Opinion dated Nov. 21, 2013 from EP No. 13004902.6.

International Preliminary Report on Patentability from corresponding PCT Application No. PCT/US2012/037744, dated Nov. 27, 2014, filed May 14, 2012.

Supplementary European Search Report from dated Jul. 24, 2015 related EP Application No. EP12876629.

Alessio; et al, "Weight-Based, Low-Dose Pediatric Whole-Body PET/CT Protocols", J Nucl Med, Oct. 2009, 50, 10, 1570-1578.

Angelini, P.,"Use of mechanical injectors during percutaneous transluminal coronary angioplasty (PTCA)," Catheterization and Cardiovascular Diagnosis, vol. 16, Issue 3, pp. 193-194, Mar. 1989.

Angiography, Catheterization and Cardiovascular Diagnosis, vol. 19, pp. 123-128, 1990.

Awai, K., et al., "Aortic and hepatic enhancement and tumor-to-liver contrast: analysis of the effect of different concentrations of contrast material at multi-detector row helical CT.," Radiology, vol. 224, Issue 3, pp. 757-763, 2002.

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

(56) References Cited

OTHER PUBLICATIONS

Bae, et al. "Aortic and Hepatic Conlrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al, "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium volume achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1899.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Beitzke, Dietrich, et al., Computed tomography angiography of the carotid arteries at low kV settings: aprospective randomised trial assessing radiation dose and diagnostic confidence, Eur Radiol, 2011.

Bischoff, Bernhard, et al., Impact of a Reduced Tube Voltage on CT Angiography and RAdiation Dose:Results of the Protection I Study, JACC Cardiovascular Imaging, 2009, pp. 940-948, vol. 2 No. 8.

Blankstein Ron; et al., "Use of 100 kV versus 120 kV in cardiac dual source computed tomography: effect onradiation dose and image quality", Int J Cardiovasc Imaging, 2011, vol. 27, pp. 579-586.

Blomley, M.J.K. and Dawson, P., "Bolus Dynamics: Theoretical and Experimental Aspects," The Brit. J. ofRadiology, vol. 70, No. 832, pp. 351-359 (Apr. 1997).

Buckley D.L. et al, "Measurement of single kidney function using dynamic contrast-enhanced MRI: comparison of two models in human subjects", Journal of Magnetic Resonance Imaging, Nov. 2006, vol. 24 Issue 5, pp. 117-123.

Buckley D.L. et al., "Measurement of single kidney function using dynamic contrast-enhanced MRI: comparison of two models in human subjects", Journal of Magnetic Resonance Imaging, Nov. 2006, vol. 24, Issue 5, pp. 1117-1123.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Cademartiri, F., et al., "Intravenous contrasts material administration at 16-detector row helical CT coronary angiography: test bolus versus bolus-tracking technique," Radiology, vol. 233, Issue 3, pp. 817-823 (Dec. 2004).

Coleman, T. and Branch, M.A., "Optimization Toolbox for Use with MATLAB, User's Guide," The Mathworks Inc., Editor (2007).

Dardik, H. et al., "Remote Hydraulic Syringe Actuator," Arch. Surg., vol. 115, Issue 1, Jan. 1980.

Dardik, H. et al., "Remote hydraulic syringe actuator: its use to avoid radiation exposure during intraoperative arteriography," Arch. Surg., vol. 115, Issue 1, pp. 105 (Jan. 1980).

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

European Search Report and Supplemental European Search Report from EP05849688 dated Mar. 21, 2014.

European Search Report dated Feb. 1, 2016 from EP15157102.

European Search Report dated Feb. 21, 2012 in European Patent Application No. 11001045.1.

European Search Report dated Jan. 30, 2003 in European Patent Application No. 02020247.9.

European Search Report dated Jun. 17, 1996 in European Patent Application No. 95202547.6.

"Extended European Search Report from EP Application No. 11798986", dated Feb. 24, 2017.

EZ CHEM Brochure, E-Z-EM, Inc. (Jul. 2007).

Farrelly, Cormac, et al., Low dose dual-souice CT angiography of the thoracic aorta, Int J Cardiovasc Imaging,2010. DOI 10.1007/s10554-010-9742-9.

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector-Row CT of The Thorax," pp. 47-59 (Jan. 22, 2004).

Fleischmann, D., "Present and Future Trends in Multiple Detector-Row CT Applications; CT Angiography", European Radiology, vol. 12, Issue 2, Supplement 2, Jul. 2002, pp. s11-s15.

Fraioli, Francesco, et al., Low-dose multidetector-row CT angiography of the infra-renal aorta and lowerextremity vessels: image quality and diagnostic accuracy in comparison with standard DSA, Eur Radiol. 2006, pp. 137-146. vol. 16.

Funama, Yoshinori, et al., Radiation Dose Reduction without Degradation of Low-Contrast Detectability atAbdominal Multisection CT with a Low-Tube Voltage Technique: Phantom Study. Radiology, Dec. 2005, pp. 905-910, vol. 237, No. 3.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, Florian W., "Performance and Sensitivity Optimization: A Vector Index Approach", Department of Systems Engineering, Case Western Reserve University, Jan. 1974.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L. et al., Physiologically Based Pharmacokinetic Modeling: Principles and Applications, Journal of Pharmaceutical Sciences, pp. 1103-1106, 1124, vol. 72, No. 10.

"Extended European Search Report from EP Application No. 18248101", dated Apr. 2, 2019.

Gerlowski L.E. and Jain R.K., "Physiologically Based Pharmacokinetic Modeling: Principles and Applications," Journal of Pharmaceutical Sciences, vol. 72, No. 10, pp. 1103-1127 (Oct. 1983).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

"Goldfarb, S., "Contrast-induced nephropathy: Risk factors, pathophysiology, and prevention," Applied Radiology (online supplement), pp. 5-16 (Aug. 2005)".

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

(56) References Cited

OTHER PUBLICATIONS

Gramovish VV., et al. Quantitative estimation of myocardial perfusion in patients with chronic ischaemic heart disease using magnetic resonance imaging, Cardiology, 2004, p. 4-12, No. 89.
Grant, Katherine, et al., Automated Dose-Optimized Selection of X-ray Tube Voltage White Paper, CARE kVSiemens, 2011.
Grant, S.C.D. et al., "Reduction of Radiation Exposure to the Cardiologist during Coronary Angiography by the Use of A Remotely Controlled Mechanical Pump for Injection of Contrast Medium," Catheterization and Cardiovascular Diagnosis, vol. 25, Issue 2, pp. 107-109 (Feb. 1992).
Guytan, A.C., "Circuitry Physiology: cardiac output and regulation", Saunders, Philadelphia, p. 173, ISBN: 07216436004, 1973.
Guytan, A.C., "Circulatory Physiology: Cardiac Output and Regulation", Saunders, Philadelphia, p. 173, ISBN: 07216436004.
Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.
Hansen, P.C., et al., "An adaptive pruning algorithm for the discrete L-curve criterion," Journal of Computational and Applied Mathematics, vol. 198, Issue 2, pp. 9 (Jan. 2007).
Hansen, P.C, Regularization tools: a MATLAB package for analysis and solution of discrete ill-posed problems, Numerical Algorithms, vol. 6, Issue 1, pp. 35, 1994.
Hansen, P.C., "The truncated SVD as a method for regularization," BIT Numerical Mathematics, vol. 27, Issue 4, pp. 534-553 (1987).
Hansen, P.C., "The truncated SVD as a method for regularization," BIT Numerical Mathematics, vol. 27, Issue 4, pp. 534-555, 1987.
Harris, P. and Heath, D. The Human Pulmonary Circulation: Its form and function in Health and Disease, 3rd Edition, Edinburgh, Churchill Livingstone, Appendix I (1986).
Harris P., H. D. "The Human Pulmonary Circulation," Edinburgh, Churchill Livingstone, (Appendix I), 1986.
Hausleiter, Jorg, et al., Radiation Dose Estimates From Cardiac Multislice Computed Tomography in DailyPractice: Impact of Different Scanning Protocols on Effective Dose Estimates, Circulation Journal of the AmericanHeart Association, Mar. 14, 2006, pp. 1304-1310, vol. 113.
Hayes, M., "Statistical Digital Signal Processing and Modeling", New York, New York, Wiley and Sons, 1996, pp. 154-177, (Prony's method).
Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.
"Infus O.R. Multi-Drug Syringe Pump with Smart Labels," Bard MedSystems Division Inc., pp. 2693-2696 (2005).
International Preliminary Examination Report and International Search Report for International Patent Application No. PCT/US00/10842 dated May 22, 2001.
International Preliminary Report on Patentability and International Search Report for International Patent Application No. PCT/US00/10842 dated May 22, 2001.
International Preliminary Report on Patentability and Written Opinion and International Search Report for International Patent Application No. PCT/US2007/026194 dated Jun. 30, 2009.
International Preliminary Report on Patentability and Written Opinion and International Search Report for International Patent Application No. PCT/US2008/067982 dated Jan. 19, 2010.
International Preliminary Report on Patentability and Written Opinion and International Search Report for International Patent Application No. PCT/US2011/041802 dated Dec. 28, 2012.
International Preliminary Report on Patentability and Written Opinion for International Patent Application No. PCT/US2007/087765 dated Jun. 30, 2009.
International Preliminary Report on Patentability and Written Opinion for International Patent Application No. PCT/US2009/047168 dated Jan. 5, 2011.
International Preliminary Report on Patentability and Wrtitten Opinion dated May 30, 2007 and International Search Report dated Sep. 25, 2006 for PCT App. No. PCT/US2005/042891.
International Preliminary Report on Patentability for International Application No. PCT/EP2005/007791, International Bureau of WIPO, Geneva, Switzerland, dated Sep. 13, 2006.
International Preliminary Report on Patentability for International Patent Application No. PCT/US2005/041913 dated May 22, 2007.
International Preliminary Report on Patentability International Search Report, and Written Opinion for International Patent Application No. PCT/US2007/026194 dated Jun. 30, 2009.
International Preliminary Report on Patentability International Search Report, and Written Opinion for International Patent Application No. PCT/US2007/087765 dated Jun. 30, 2009.
International Preliminary Report on Patentability International Search Report, and Written Opinion for International Patent Application No. PCT/US2008/067982 dated Jan. 19, 2010.
International Preliminary Report on Patentability International Search Report, and Written Opinion for International Patent Application No. PCT/US2009/047168 dated Jan. 5, 2011.
International Preliminary Report on Patentability, International Search Report and Written Opinion for International Patent Application No. PCT/US2011/041802 dated Dec. 28, 2012.
International Preliminary Report on Patentability, International Search Report, and Wrtitten Opinion for International Patent Application No. PCT/US2005/042891 dated May 30, 2007.
International Search Report and the Written Opinion of the International Searching Authority for application No. PCT/US2007/26194 dated Jun. 26, 2008.
International Search Report and Written Opinion for International Application No. PCT/US05/42891, ISA/US dated Sep. 25, 2006.
International Search Report and Written Opinion for International Patent Application No. PCT/US2005/041913 dated May 24, 2006.
International Search Report and Written Opinion from counterpart PCT Application PCT/2008/67982 filed Jun. 24, 2008.
International Search Report for International Patent Application No. PCT1US20081067982 dated Oct. 8, 2008.
International Search Report for International Patent Application No. PCT1US2009/047168 dated Aug. 4, 2009.
International Search Report for International Patent Application No. PCT/US2000/010842 dated Apr. 5, 2001.
International Search Report for International Patent Application No. PCT/US2000/010842 dated Jan. 23, 2001.
International Search Report for International Patent Application No. PCT/US2007/026194 dated Jun. 26, 2008.
International Search Report for International Patent Application No. PCT/US2007/087765 dated Jun. 12, 2008.
International Search Report for International Patent Application No. PCT/US2011/041802 dated Jan. 5, 2012.
International Search Report for International Patent Application No. PCT/US96/15680 dated Jan. 28, 1997.
Ireland, M.A., et al., "Safety and Convenience of a Mechanical Injector Pump for Coronary Angiography," Catheterization and Cardiovascular Diagnosis, vol. 16, Issue 3, pp. 199-201 (1989).
ISTAT 1 System Manual, Abbott Laboratories, Rev. Aug. 14, 2006.
I-STAT Analyzer System, Abbott Laboratories, product data from corporate website (www.abbottpointofcoare.com) Retrieved on Oct. 28, 2009.
Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).
Jo, S.H., et al., "Renal Toxicity Evaluation and Comparison Between Visipaque (Iodixanol) and Hexabrix (Ioxaglate) in Patients With Renal Insufficiency Undergoing Coronary Angiography: the RECOVER study: a randomized controlled trial," Journal of the American College of Cardiology, vol. 48, Issue 5, pp. 924-930 (Sep. 2006).
Kalafut, J.S., "A New Paradigm for the Personalized Delivery of Iodinated Contrast Material at Cardiothoracic, Computed Tomography Angiography," Doctoral Dissertation, University of Pittsburgh (2010).

(56) References Cited

OTHER PUBLICATIONS

KalRA, Mannudeep, et al., Clinical Comparison of Standard Dose and 50% Reduced-Dose Abdominal CT: Effecton Image Quality, American Journal of Radiology, Nov. 2002, pp. 1101-1106. vol. 179.
Kayan, Mustafa, et al., Carotid CT-angiography: Low versus standard volume contrast media and low kVprotocol for 128-slice MDCT, European Journal of Radiology, 2012, pp. 2144-2147, vol. 81.
Koh, T.S., et al., "Assessment of Perfusion by Dynamic Contrast-Enhanced Imaging Using a Deconvolution ApproachBased on Regression and Singular Value Decomposition," IEEE Transactions on Medical Imaging, vol. 23, Issue 12,pp. 1532-1542 (Dec. 2004).
Korosec, F.R., "Basic Principles of Phase-contrast, Time-of-flight, and Contrast-enhanced MR Angiography," Principles of MR Angiography, pp. 1-10 (1999).
Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.
Korosec, Frank, "Basic Principles of Phase-contrast, Time-of-flight, and Contrast-enhanced MR Angiography", 1999.
Krause, W, "Application of pharmacokinetics to computed tomography: injection rates and schemes: mono-, bi-, or multiphasic?," Investigative Radiology, vol. 31, Issue 2, pp. 91-100, Feb. 1996.
Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).
Leschka, Sebastian, et al., Low kilovoltage cardiac dual-source CT: attenuation, noise, and radiation dose, EurRadiol. 2008, pp. 1809-1817, vol. 18.
Liebel-Flarsheim company—Angiomat 6000 Digital Injection System Operator's Manual, 600950 Rev 1 (1990); p. 3-6 to 3-8, 4-52 to 4-56.
Liebel-Flarsheim Company, "Angiomat 6000 Digital Injection System—Operator's Manual", Document No. 600950, Rev. 1, Jan. 1990.
Liebel-Flarsheim company,Angiomat 6000 Digital Injection System Operator's Manual, 600950 Rev 1 (1990); pp. 1-1 to 9-6.
Mahnken, A. H., et al., "Determination of cardiac output with multislice spiral computed tomography: a validation study," Investigative Radiology, vol. 39, Issue 8, pp. 451-454, Aug. 2004.
Mahnken, A. H., et al., "Measurement of cardiac output from a test-bolus injection in multislice computed tomography," European Radiology, vol. 13, Issue 11, pp. 2498-2504, 2003.
Marin, Daniele, et al., Low-Tube-Voltage, High-Tube-Current Multidetector Abdominal CT: Improved ImageQuality and Decreased Radiation Dose with Adaptive Statistical Iterative Reconstruction algorithm—Initial ClincalExperience, Radiology. Jan. 2010, pp. 145-153, vol. 254, No. 1.
Mark V/Mark V Plus Injector Operation Manual KMP 805P Rev. B. Medrad, Inc, 1990.
McClellan, J.H., "Parametric Signal Modeling," Chapter 1 in Advanced Topics in Signal Processing, Pentice-Hall, Englewood Cliffs, NJ (1988).
McCullough, P.A., et al., "Contrast-Induced Nephropathy (CIN) Consensus Working Panel: Executive Summary,"Reviews in Cardiovascular Medicine, vol. 7, Issue 4, pp. 177-197 (2006).
MCT and MCT Plus Injection Systems Operation Manual KMP 810P, Medrad, Inc, 1991.
Medrad, Mark V/Mark V Plus Injector Operation Manual,KMP 805P Rev. B (1990); pp. 1-18 to 1-28, 3-7 to 3-13, 14-1 to 14-4.
Nakayama, Yoshiharu, et al., Abdominal CT with Low Tube Voltage: Preliminary Observations about RadiationDose, Contrast Enhancement, Image Quality, and Noise, Radiology, Dec. 2005, pp. 945-951, vol. 237, No. 3.

Neatpisarnvanit, C. and Boston, J.R., "Estimation of plasma insulin from plasma glucose", IEEE Transactions on Biomedical Engineering, vol. 49, Issue 11, pp. 1253-1259, 2002.
Newton, Texas A&M University lecture slides, Statistics 626, 1999.
O'Connor, Owen, et al., Development of Low-Dose Protocols for Thin-Section CT Assessment of Cystic Fibrosisin Pediatric Patients, Radiology, Dec. 2010, pp. 820-829, vol. 257, No. 3.
Ostergaard, L., et al., "High resolution measurement of cerebral blood flow using intravascular tracer boluspassages. Part 1: Mathematical approach and statistical analysis," Magnetic Resonance in Medicine, vol. 36, Issue 5,pp. 715-725 (Nov. 1996).
Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).
Parker, K.J., et al., "A Particulate Conlrast Agent With Potential For Ultrasound Imaging of Liver," Ultrasound in Medicine & Biology, vol. 13, Issue 9, pp. 555-566 (Sep. 1987).
PHYSBE a classic model of the human circulatory system available from The Math Works, Inc. of Natick, Massachusetts, accessed at www.mathworks.com/products/demos/simulink/physbe, May 31, 2005, pp. 11.
Regression Analysis Tutorial, Econometrics Laboratory, University of California at Berkeley, Mar. 22-26, 1999, pp. 183-201.
Renalguard, PLC Medical Systems, Inc. News Release. (May 12, 2008).
"Renalguard," PLC Medical Systems, Inc. News Release, pp. 1-3 (May 12, 2008).
Renalguard, PLC Medical Systems, Inc., product data from corporate website (www.plcmed.com) Retrieved on Oct. 28, 2009.
Rosen, B.R. et al., "Perfusion Imaging with NMR Contrast Agents," Magentic Resonance in Medicine, vol. 14, No. 2, pp. 249-265, May 1, 1990.
Sablayrolles, J-L, "Cardiac CT: Experience from Daily Practice", Advance CT, a GE Healthcare Publication. Aug. 2004.
Sablayrolles, J-L, "Cardiac CT: Experience from Daily Practice," Advance CT, a GE Healthcare Publication, pp. 1-10 (Aug. 2004).
Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.
Suess, Christoph, et al, Dose optimization in pediatric CT: current technology and future innovations. PediatricRadiology, 2002, pp. 729-734. vol. 32.
Sung, C.K., et al., "Urine Attenuation Ratio: A Mew CT Indicator or Renal Artery Stenosis," AJR Am J Roentgenol,vol. 187, Issue 2, pp. 532-540 (Aug. 2006).
Supplementary European Search Report dated Apr. 15, 2011 in European Patent Application No. 07867951.1.
Supplementary European Search Report dated Aug. 19, 2010 in European Patent Application No. 05852259.0.
Supplementary European Search Report dated Dec. 9, 1998 in European Patent Application No. 96936079.0.
Supplementary European Search Report dated Jul. 23, 2013 in European Patent Application No. 08771789.8.
The European Search Report from EP14174725.3 dated May 8, 2015.
"The Solution for Your IV Formulas", Valley Lab. Inc., E-39-15, 3399, 3400, 2646.
"Supplementary Partial European Search Report in EP Application No. EP11798986", dated Nov. 10, 2016.
Kai; Gao, "Study on the Correlation between X-ray Image Quality and Radiation Dose and Contrast Agent Concentration", May 1, 2005.

\* cited by examiner

Cardiac w/Bolus Tracking

| Calculation Inputs | Active | | Cancel | OK |
|---|---|---|---|---|
| Patient Weight | 75 - 94 kg | | Notice | |
| Concentration | 370 mgI/ml | | | |
| Tube Voltage | 120 kVp | | | |

Instructions:

For highlighted items, select either Preset or Current Values or manually select a new value by clicking on the button in the Active column.

Load syringes at any time by clicking "OK" to return to the main screen.

Basic View shows parameters that must be entered only.

Advanced View

Parameter Description

FIG. 3

Select Protocol...                                    Cancel | Select

Details

Flow Rate (ml/s)    Volume (ml)
Ⓐ   3              75
Ⓑ   3              30

Diagnostic Contrast Volume    75
Diagnostic Saline Volume      30

Head Protocol 1    kVp

→

Current
Head | Neck | Chest | Abdomen | Pelvis | Extremities
View All

FIG. 17

Select Protocol...

Current

- Chest Protocol 1
- P₃T Dr A's Cardiac
- P₃T Cardiac w/ Bolus Tracking  kVp

Head | Neck | Chest | Abdomen | Pelvis | Extremities

View All

Details

| | |
|---|---|
| Contrast Conc: | 370 mgI/ml |
| Test Injection: | Yes |
| Transit Bolus: | No |
| Max Flow Rate: | 8 ml/s |
| Adjusted Duration: | 00:04 |
| Min Injection Duration: | 00:16 |
| Pressure Limit: | 325 psi |
| Weight Units: | kg |

Cancel | Select

Head Protocol 1

Calculation Inputs

[X] kVp  Tube Voltage

Active 120 kVp

Cancel | OK

Tube Voltage
(select one)

Clear 80 kVp 100 kVp 120 kVp 140 kVp

Cancel | Entry

Description of Tube Voltage parameter and how it affects the clinical rule.

FIG. 19

Cardiac w/Bolus Tracking

Calculation Inputs     Active

Patient Weight     75 - 94 kg

Concentration     370 mg/ml

[X] kVp Tube Voltage     120 kVp

Cancel     OK

Tube Voltage (select one)

Clear 80 kVp 100 kVp 120 kVp 140 kVp

Cancel     Entry

Description of Tube Voltage parameter and how it affects the clinical rule.

FIG. 20

Head Protocol 1

Calculation Inputs | Active

[X] kVp  Tube Voltage | 100 kVp

Description of Tube Voltage parameter and how it affects the clinical rule.

[ Cancel ] [ OK ]

Notice

Tube Voltage:
Decrease contrast 19%.

Instructions:

For highlighted items, select either Preset or Current values, or manually select a new value by clicking on the button in the Active column.

Load syringes at any time by clicking "OK" to return to the main screen.

Basic View shows parameters that must be entered only.

[ Advanced View ]

FIG. 21

Cardiac w/Bolus Tracking

| Calculation Inputs | Active |
|---|---|
| Patient Weight | 40 59 kg |
| Concentration | 350 mg/ml |

[X] kVp  Tube Voltage  | 100 kVp

Notice

Tube Voltage: Decrease contrast 19%.

Instructions:

For highlighted items, select either Preset or Current values, or manually select a new value by clicking on the button in the Active column.

Load syringes at any time by clicking "OK" to return to the main screen.

Basic View shows parameters that must be entered only.

[ Advanced View ]

[ Cancel ]  [ OK ]

Description of Tube Voltage parameter and how it affects the clinical rule.

Flow Chart for Creation of Injection Protocol Using Adjusted Dosing Factors

SYSTEMS AND METHODS FOR DETERMINATION OF PHARMACEUTICAL FLUID INJECTION PROTOCOLS BASED ON X-RAY TUBE VOLTAGE

The present application is a 35 U.S.C. § 120 continuation application of U.S. patent application Ser. No. 14/401,330, filed Nov. 14, 2014, which is a 35 U.S.C. § 371 national phase application of PCT/US12/37744, filed on May 14, 2012, the entire contents of which are incorporated by reference herein.

RELATED APPLICATIONS

This application contains subject matter that may be related to that disclosed and/or claimed in U.S. Pat. No. 7,925,330, filed on Mar. 27, 2007, United States Patent Application Publication Numbers 2007/0213662, filed on Mar. 27, 2008; 2007/0255135, filed Mar. 27, 2007; 2008/0097197, filed Mar. 22, 2007; 2010/0030073, filed on Jun. 12, 2009; 2010/0113887, filed on Jun. 15, 2009; 2010-0204572, filed on Jan. 15, 2010; and International Patent Application Publication Numbers WO/2006/058280 (International Patent Application No. PCT/US05/042891), filed on Nov. 23, 2005, and WO/2006/055813 (International Patent Application No. PCT/US2005/041913), filed on Nov. 16, 2005, the disclosures of which are incorporated herein by reference and made a part hereof.

BACKGROUND OF THE INVENTION

Field of the Invention

The present invention is related to devices, systems and methods for fluid delivery, and, particularly, to devices, systems and methods for delivery of a pharmaceutical fluid to a patient, and, especially for delivery of a contrast medium to a patient during a medical injection procedure for diagnostic and/or therapeutic reasons.

Description of Related Art

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. The disclosure of all references cited herein is incorporated by reference.

The administration of contrast medium with, for example, a power injector for radiological exams typically starts with the clinician filling an empty, disposable syringe with a certain volume of contrast agent pharmaceutical. In other procedures, a syringe pre-filled with contrast agent may be used. The clinician then determines a volumetric flow-rate and a volume of contrast to be administered to the patient to enable a diagnostic image. An injection of saline solution, having a volume and flow rate determined by the operator, often follows the administration of contrast agent into the veins or arteries. A number of currently available injectors allow for the operator to program a plurality of discrete phases of volumetric flow rates and volumes to deliver. For example, the SPECTRIS SOLARIS® and STELLANT® injectors available from MEDRAD, INC., a business of Bayer HealthCare, provide for entry of up to and including six discrete pairs or phases of volumetric flow rate and volume for delivery to a patient (for example, for contrast and/or saline). Such injectors and injector control protocols for use therewith are disclosed, for example, in U.S. Pat. No. 6,643,537 and Published U.S. Patent Application Publication No. 2004/0064041, assigned to the assignee of the present invention, the disclosures of which are incorporated herein by reference. The values or parameters within the fields for such phases are generally entered manually by the operator for each type of procedure and for each patient undergoing an injection/imaging procedure. Alternatively, earlier manually entered values of volume and flow rate can be stored and later recalled from the computer memory. However, the manners in which such parameters are to be determined and tailored for a specific procedure for a specific patient are not well developed.

In this regard, differences in contrast dosing requirements for different patients during imaging and other procedures have been recognized. For example, U.S. Pat. No. 5,840,026, assigned to the assignee of the present invention, the disclosure of which is incorporated herein by reference, discloses devices and methods to customize the injection to the patient using patient specific data derived before or during an injection. Although differences in dosing requirements for medical imaging procedures based upon patient differences have been recognized, conventional medical imaging procedures continue to use pre-set doses or standard delivery protocols for injecting contrast media during medical imaging procedures. Given the increased scan speed of recently available CT scanners including MDCT (or MSCT) scanners, single phase injections are dominant over biphasic or other multiphasic injections in regions of the world where such fast scanners are used. Although using standard, fixed or predetermined protocols (whether uniphasic, biphasic or multiphasic) for delivery simplifies the procedure, providing the same amount of contrast media to different patients under the same protocol can produce very different results in image contrast and quality. Furthermore, with the introduction of the newest MDCT scanners, an open question in clinical practice and in the CT literature is whether the standard contrast protocols used with single-slice, helical scanners will translate well to procedures using the MDCT machines. See, for example, Cademartiri, F. and Luccichenti, G., et al., "Sixteen-row multi-slice computed tomography: basic concepts, protocols, and enhanced clinical applications." Semin Ultrasound CT MR 25(1): 2-16 (2004).

A few studies have attempted quantitative analyses of the injection process during CT angiography (CTA) to improve and predict arterial enhancement. For example, Bae and coworkers developed pharmacokinetic (PK) models of the contrast behavior and solved the coupled differential equation system with the aim of finding a driving function that causes the most uniform arterial enhancement. K. T. Bae, J. P. Heiken, and J. A. Brink, "Aortic and hepatic contrast medium enhancement at CT. Part I. Prediction with a computer model," Radiology, vol. 207, pp. 647-55 (1998); K. T. Bae, "Peak contrast enhancement in CT and MR angiography: when does it occur and why? Pharmacokinetic study in a porcine model," Radiology, vol. 227, pp. 809-16 (2003); K. T. Bae et al., "Multiphasic Injection. Method for Uniform Prolonged Vascular Enhancement at CT Angiography: Pharmacokinetic Analysis and Experimental Porcine Method," Radiology, vol. 216, pp. 872-880 (2000); U.S. Pat. Nos. 5,583,902, 5,687,208, 6,055,985, 6,470,889 and 6,635,030, the disclosures of which are incorporated herein by reference. An inverse solution to a set of differential equations of a simplified compartmental model set forth by Bae et al. indicates that an exponentially decreasing flow rate of contrast medium may result in optimal/constant enhancement in a CT imaging procedure. However, the injection profiles computed by inverse solution of the PK model are profiles not readily realizable by most CT power injectors without major modification.

In another approach, Fleischmann and coworkers treated the cardiovascular physiology and contrast kinetics as a "black box" and determined its impulse response by forcing the system with a short bolus of contrast (approximating a unit impulse). In that method, one performs a Fourier transform on the impulse response and manipulates this transfer function estimate to determine an estimate of a more optimal injection trajectory than practiced previously. D. Fleischmann and K. Hittmair, "Mathematical analysis of arterial enhancement and optimization of bolus geometry for CT angiography using the discrete Fourier transform," J. Comput. Assist Tomogr., vol. 23, pp. 474-84 (1999), the disclosure of which is incorporated herein by reference.

Uniphasic administration of contrast agent (typically, 100 to 150 mL of contrast at one flow rate) results in a non-uniform enhancement curve. See, for example, D. Fleischmann and K. Hittmair, supra; and K. T. Bae, "Peak contrast enhancement in CT and MR angiography: when does it occur and why? Pharmacokinetic study in a porcine model," Radiology, vol. 227, pp. 809-16 (2003), the disclosures of which are incorporated herein by reference. Fleischmann and Hitmair thus presented a scheme that attempted to adapt the administration of contrast agent into a biphasic injection tailored to the individual patient with the intent of optimizing imaging of the aorta. A fundamental difficulty with controlling the presentation of CT contrast agent is that hyperosmolar drug diffuses quickly from the central blood compartment. Additionally, the contrast is mixed with and diluted by blood that does not contain contrast.

Fleischmann proscribed that a small bolus injection, a test bolus injection, of contrast agent (16 ml of contrast at 4 ml/s) be injected prior to the diagnostic scan. A dynamic enhancement scan was made across a vessel of interest. The resulting processed scan data (test scan) was interpreted as the impulse response of the patient/contrast medium system. Fleischmann derived the Fourier transform of the patient transfer function by dividing the Fourier transform of the test scan by the Fourier transform of the test injection. Assuming the system was a linear time invariant (LTI) system and that the desired output time domain signal was known (a flat diagnostic scan at a predefined enhancement level) Fleischmann derived an input time signal by dividing the frequency domain representations of the desired output by that of the patient transfer function. Because the method of Fleischmann et al. computes input signals that are not realizable in reality as a result of injection system limitations (for example, flow rate limitations), one must truncate and approximate the computed continuous time signal.

In addition, to control a powered injector to provide a desired time enhancement curve, the operation of a powered injector should be carefully controlled to ensure the safety of the patient. For example, it is desirable not to exceed a certain fluid pressure during an injection procedure. In addition to potential hazards to the patient (for example, vessel damage) and potential degradation of the diagnostic and/or therapeutic utility of the injection fluid, excessive pressure can lead to equipment failure. Disposable syringes and other fluid path components (sometimes referred to collectively as a "disposable set") are typically fabricated from plastics of various burst strengths. If the injector causes pressure in the fluid path to rise above the burst strength of a disposable fluid path element, the fluid path element will fail.

In addition to problems of control with current injector systems, many such systems lack convenience and flexibility in the manner in which the injector systems must be operated. In this regard, the complexity of medical injection procedures and the hectic pace in all facets of the health care industry place a premium on the time and skills of an operator.

Although advances have been made in the control of fluid delivery systems to, for example, provide a desirable time enhancement curve and to provide for patient safety, it remains desirable to develop improved devices, systems, and method for delivery of fluids to a patient.

SUMMARY OF THE INVENTION

In one aspect of the invention, provided is a system for patient imaging including an imaging system and a parameter generator to determine parameters of at least a first phase of an injection procedure, wherein the imaging system comprises a scanner comprising at least one x-ray tube and wherein the parameter generator is programmed to determine at least one of the parameters on the basis of a voltage to be applied to the at least one x-ray tube during an imaging procedure. The scanner may be a CT scanner, which may be programmable to operate at different x-ray tube voltages.

In certain embodiments, the parameter generator of the system can be in communicative connection with the imaging system. In certain embodiments, the parameter generator can be integrated into the imaging system.

In some non-limiting embodiments, the system can further include an injector system, and the injector system can include at least one pressurizing mechanism, at least one fluid container operably associated with the at least one pressurizing mechanism, one of the fluid containers adapted to contain a contrast enhancing agent and one of the fluid containers adapted to contain a diluent, and a controller operably associated with the at least one pressurizing mechanism.

In certain embodiments, the parameter generator can be in communicative connection with at least one of the imaging system and the controller of the injector system, and in certain embodiments, the parameter generator can be integrated into the injector system.

In some non-limiting embodiments, the parameter generator can be programmed to determine at least one of a volume of a pharmaceutical fluid to be injected during at least the first phase and a flow rate of the pharmaceutical fluid to be injected during at least the first phase on the basis of the voltage to be applied to the at least one x-ray tube during the imaging procedure. The pharmaceutical fluid may include a contrast enhancing agent.

In certain non-limiting embodiments, the parameter generator can be programmed to determine the volume of the pharmaceutical fluid to be injected during at least the first phase according to the formula: $V_1 = \text{weight} * X * Y$, wherein $V_1$ is the volume of the pharmaceutical fluid, X is a function of patient weight and x-ray tube voltage, and Y is a function of the concentration of a contrast enhancing agent in the pharmaceutical fluid. The parameter generator may be programmed to determine X for a particular patient weight from a look-up table wherein X is set forth as a function of patient weight and the voltage to be applied to the at least one x-ray tube during the imaging procedure.

In some non-limiting embodiments, the parameter generator can be programmed to determine at least a first flow rate of the pharmaceutical fluid by dividing $V_1$ by an injection duration of the first phase. The parameter generator may be programmed to determine the injection duration on the basis of one or more criteria inputted by an operator, which criteria can include at least an identification of a body region to be imaged during the imaging procedure.

In certain non-limiting embodiments, the parameter generator can be further programmed to determine a volume $V_2$ of pharmaceutical fluid to be delivered in at least a second phase of the injection procedure in which both the pharmaceutical fluid and a diluent are to be delivered.

In some non-limiting embodiments, the parameter generator can be programmed to determine the volume of the pharmaceutical fluid to be injected during at least the first phase by adjusting a volume parameter of a baseline injection protocol. Data representing the baseline injection protocol can exists in memory of the system or accessible to the system. The parameter generator can also be programmed to determine the baseline injection protocol on the basis of one or more criteria inputted by an operator. In certain embodiments, the parameter generator can be programmed to determine the volume of the pharmaceutical fluid to be injected during at least the first phase by applying a tube voltage modification factor to the volume parameter of the baseline injection protocol.

In some non-limiting embodiments, the parameter generator can be programmed to determine the flow rate of the pharmaceutical fluid to be injected during at least the first phase by adjusting a flow rate parameter of a baseline injection protocol. Data representing the baseline injection protocol can exists in memory of the system or accessible to the system. The parameter generator can also be programmed to determine the baseline injection protocol on the basis of one or more criteria inputted by an operator. In certain embodiments, the parameter generator can be programmed to determine the flow rate of the pharmaceutical fluid to be injected during at least the first phase by applying a tube voltage modification factor to the flow rate parameter of the baseline injection protocol.

In another aspect, provided is a parameter generator for use in an imaging system comprising a scanner comprising at least one x-ray tube, wherein the parameter generator is programmed to determine parameters of at least a first phase of an injection procedure including at least one parameter on the basis of a voltage to be applied to the at least one x-ray tube during an imaging procedure.

In another non-limiting embodiment, provided is a method of controlling an injector system for delivering a pharmaceutical fluid to a patient as part of an imaging procedure, the injector system in operative connection with an imaging system comprising a scanner comprising at least one x-ray tube. The steps of the method include: determining, using a parameter generator, injection parameters of at least a first phase of an injection procedure, wherein at least one of the injection parameters is determined on the basis of a voltage to be applied to the at least one x-ray tube during the imaging procedure; and controlling the injector system at least in part on the basis of the determined injection parameters.

In some non-limiting embodiments of the method, the injection parameters that are determined include at least one of a volume of the pharmaceutical fluid to be injected during at least the first phase of the injection procedure and a flow rate of the pharmaceutical fluid to be injected during at least the first phase of the injection procedure. The volume of the pharmaceutical fluid to be injected during at least the first phase can be determined according to the formula: $V_1$=weight*X*Y, wherein $V_1$ is the volume of the pharmaceutical fluid, X is a function of patient weight and x-ray tube voltage, and Y is a function of the concentration of a contrast enhancing agent in the pharmaceutical fluid. In certain embodiments, X is determined for a particular patient weight from a look-up table wherein X is set forth as a function of patient weight and the voltage to be applied to the at least one x-ray tube during the imaging procedure.

In certain non-limiting embodiments of the method, at least a first flow rate of the pharmaceutical fluid is determined by dividing $V_1$ by an injection duration of the first phase. The injection duration of the first phase can be inputted by an operator using a graphical user interface. The injection duration can also be determined by the parameter generator on the basis of one or more criteria inputted by an operator.

In some non-limiting embodiments of the method, the volume of the pharmaceutical fluid to be injected during at least the first phase is determined by adjusting a volume parameter of a baseline injection protocol. Data representing the baseline injection protocol can be recalled from memory associated with or accessible by at least one of the injector system, the imaging system, and the parameter generator. The baseline injection protocol may also be determined on the basis of one or more criteria inputted by an operator. The volume of the pharmaceutical fluid to be injected during at least the first phase of the injection procedure can be determined by applying a tube voltage modification factor to the volume parameter of the baseline injection protocol.

In certain non-limiting embodiments of the method, the flow rate of the pharmaceutical fluid to be injected during at least the first phase is determined by adjusting a flow rate parameter of a baseline injection protocol. Data representing the baseline injection protocol can be recalled from memory associated with or accessible by at least one of the injector system, the imaging system, and the parameter generator. The baseline injection protocol can be determined on the basis of one or more criteria inputted by an operator. The flow rate of the pharmaceutical fluid to be injected during at least the first phase can be determined by applying a tube voltage modification factor to the flow rate parameter of the baseline injection protocol.

In some non-limiting embodiments of the method, the method can further include the step of populating the determined injection parameters on a graphical user interface associated with at least one of the injector system and the imaging system.

In another aspect, provided is a method of generating an injection protocol for use with an injector system in operative connection with an imaging system comprising a scanner comprising at least one x-ray tube, the method including the step of determining, using a parameter generator, injection parameters of at least a first phase of an injection procedure, wherein at least one of the injection parameters is determined on the basis of a voltage to be applied to the at least one x-ray tube during an imaging procedure.

The present invention, along with the attributes and attendant advantages thereof, will best be appreciated and understood in view of the following detailed description taken in conjunction with the accompanying drawings.

BRIEF DESCRIPTION OF THE DRAWINGS

FIG. 3 illustrates an embodiment of a graphical interface from which an operator can enter variables related to a particular imaging procedure.

FIG. 17 illustrates an embodiment of a graphical interface from which an operator can choose a vascular region of interest and baseline protocol for imaging.

FIG. 18 illustrates another embodiment of a graphical interface from which an operator can choose a vascular region of interest and baseline protocol for imaging.

FIG. 19 illustrates an embodiment of a graphical interface from which an operator can choose a tube voltage value.

FIG. 20 illustrates an embodiment of a graphical interface from which an operator can choose a tube voltage value along with other variables of an injection procedure.

FIG. 21 illustrates another portion of a graphical interface for use with an embodiment of a parameter generation system.

FIG. 22 illustrates another portion of a graphical interface for use with an embodiment of a parameter generation system.

FIG. 24 illustrates another embodiment of a graphical interface which presents an operator with a computed injection protocol.

DETAILED DESCRIPTION OF THE
PREFERRED EMBODIMENTS

As used herein with respect to an injection procedure, the term "protocol" refers to a group of parameters such as flow rate, volume to be injected, injection duration, etc. that define the amount of fluid(s) to be delivered to a patient during an injection procedure. Such parameters can change over the course of the injection procedure. As used herein, the term "phase" refers generally to a group of parameters that define the amount of fluid(s) to be delivered to a patient during a period of time (or phase duration) that can be less than the total duration of the injection procedure. Thus, the parameters of a phase provide a description of the injection over a time instance corresponding to the time duration of the phase. An injection protocol for a particular injection procedure can, for example, be described as uniphasic (a single phase), biphasic (two phases) or multiphasic (two or more phases, but typically more than two phases). Multiphasic injections also include injections in which the parameters can change continuously over at least a portion of the injection procedure.

Figure 1:
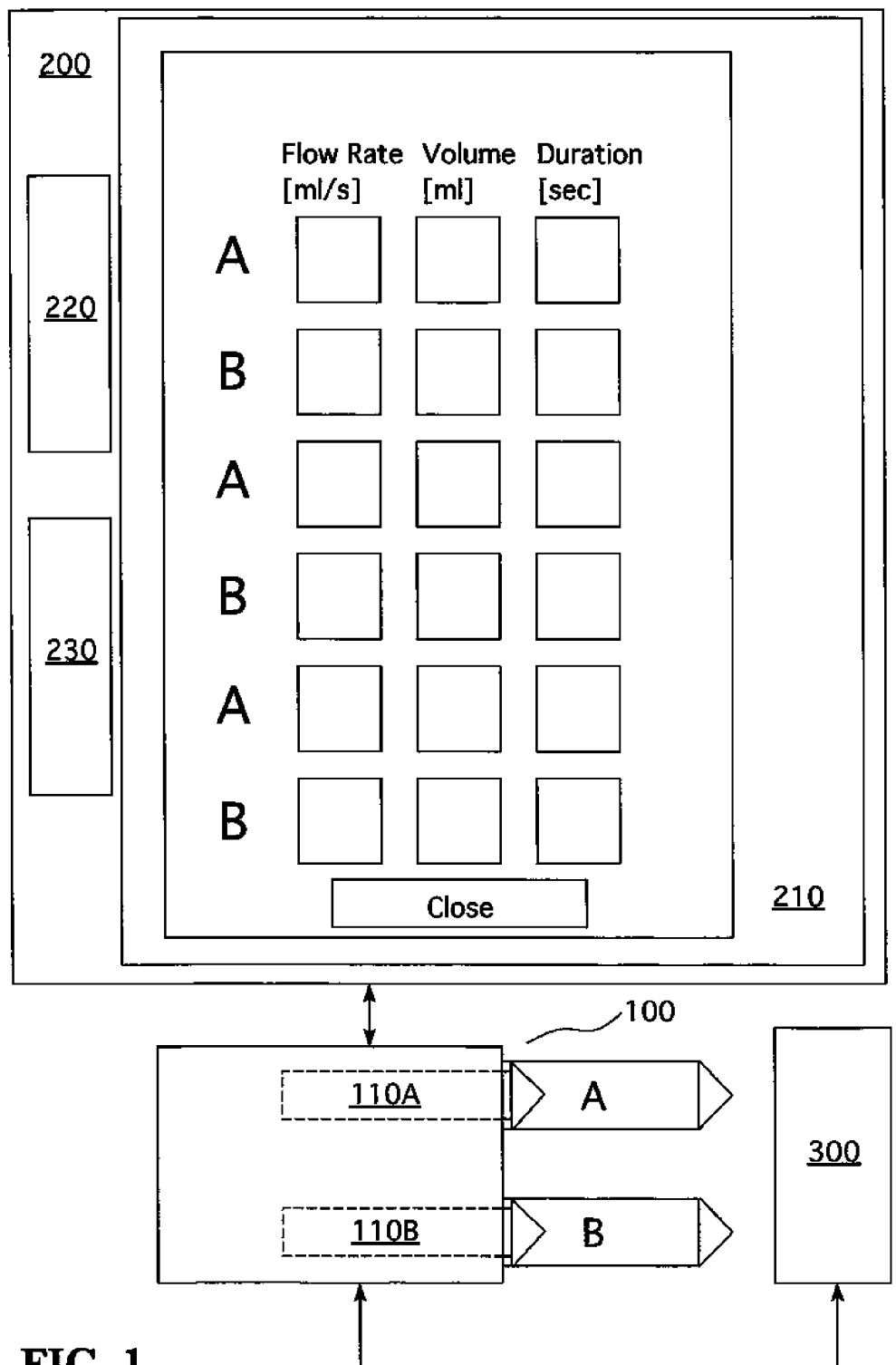
FIG. 1 illustrates an embodiment of a multi-phasic Graphical User Interface (GUI) for use in setting forth parameters for a plurality of phases for a two-syringe injector also illustrated in FIG. 1.

In several embodiments, an injector system (such as a dual syringe injector system 100 as illustrated in FIG. 1 and as, for example, disclosed in U.S. Pat. No. 6,643,537 and U.S. Patent Application Publication No. 2004/0064041) may be used to implement the concepts described in detail herein, and typically includes two fluid delivery sources (sometimes referred to as source "A" and source "B" herein, such as syringes) that are operable to introduce a first fluid and/or a second fluid (for example, contrast medium, saline/diluent, etc.) to a patient independently (for example, simultaneously, simultaneously in different volumetric flow proportion to each other, or sequentially or subsequent to each other (that is, A then B, or B then A)).

In the embodiment of FIG. 1, source A is in operative connection with a pressurizing mechanism such as a drive member 110A, and source B is in operative connection with a pressurizing mechanism such as a drive member 110B. Source A and source B can each be, for example, a fluid container. The injector system 100 includes a controller 200 in operative connection with injector system 100 and drive members 110A and 110B that is operable to control the operation of drive members 110A and 110B to control injection of fluid A (for example, contrast medium) from source A and injection of fluid B (for example, saline/diluent) from source B, respectively. Controller 200 can, for example, include a user interface comprising a display 210.

Controller 200 can also include a processor 220 (for example, a digital microprocessor as known in the art) in operative connection with a memory 230. The system can further include an imaging system 300. Imaging system 300 can, for example, be a Computed Tomography (CT) system or another tomographic imaging system. The injector system 100 can be in communicative connection with imaging system 300, and one, a plurality or all the components of the injector system 100 and imaging system 300 can be integrated into a single device.

One example of an imaging system 300 is a CT system. A CT system typically includes a scanner which employs x-rays to create an image utilizing the principle of attenuation. Attenuation represents a measure of the gradual loss in intensity of a flux, such as an x-ray, as it passes through a medium, such as the tissue, bone and other materials of the body. CT systems generally include an x-ray source, typically an x-ray tube or tubes, and one or more x-ray sensors located opposite the x-ray source for capturing the attenuated x-rays after they pass through the body, including body structures that may be filled with a contrasting agent.

With respect to x-ray imaging techniques using iodine-based contrast agents, the attenuation and absorption of x-ray photons passing through body structures filled with iodinated contrast material increases as the voltage applied to the x-ray source (e.g., x-ray tubes) decreases. The increase in attenuation is believed to be due to the dominance of photo-electric absorption at the lower x-ray excitation energies, especially as one approaches the K-Shell absorption peak of iodine. The following table (Table 1) reflects an art-recognized relationship between x-ray tube voltage and the attenuation to contrast concentration ratio (aka, k-factor). (See Takanami, et al. 2008).

TABLE 1

Tube Voltage to K-Factor Relationship

| Tube Voltage ($kV_p$) | K-Factor ($HU/(mgI \cdot mL^{-1})$) |
|---|---|
| 80 | 41 |
| 100 | 31 |
| 120 | 25 |
| 140 | 21 |

Because the attenuation to contrast concentration ratio varies based on the voltage being applied to the x-ray tube, all else being equal, two scans carried out using the same contrast concentration at different x-ray tube voltages will produce different images. In particular, in the resulting imagery created by a CT system, an increased attenuation creates a brighter opacification and greater image contrast between the contrast-filled structures and the surrounding tissue. Because the opacification can increase as the tube voltage decreases, the volume of contrast needed to achieve sufficient contrast opacification in a territory of interest can be reduced by using lower tube voltages. Similarly, because the opacification can decrease as the tube voltage increases, a greater volume of contrast may be needed to achieve sufficient contrast opacification and adequate imaging where higher tube voltages are being used during the scanning procedure.

The present disclosure provides methods, systems, and algorithms for generating phase parameters predetermined as being effective for the type of imaging procedure being performed that are based, at least in part, on the tube voltage that will be applied during the imaging procedure. Tailoring the phase parameters to account for tube voltage has been found to not only lead to contrast savings, but also help to avoid less than ideal enhancement outcomes for higher tube voltages where the $HU/(mgI.mL^{-1})$ ratio is smaller. Such phase parameters can be established in a variety of ways, including through the collection of patient data over time (by, for example, employing artificial intelligence techniques, statistical means, adaptive learning methodologies, etc.), through mathematical modeling, through the modification of baseline or known protocols to account for variations in the tube voltage values, or otherwise.

In certain non-limiting embodiments, injection phase parameters as described above are populated within a phase programming mechanism, or parameter generator, which may be a computer having software installed thereon for implementing the methods described herein, based on one or more parameters of interest including, but not limited to, contrast agent concentration (for example, iodine concentration in the case of a CT procedure), a patient parameter (for example, body weight, height, gender, age, cardiac output, etc.) the type of scan being performed, the type of catheter inserted into the patient for intravascular access, and the voltage being applied when performing the imaging scan (for example, the voltage being applied to one or more x-ray tubes during a CT scan). The parameter generator is typically in communicative connection with at least one of the imaging system 300 and the injector system 100. The parameter generator can also include a processor (for example, a digital microprocessor as known in the art) in operative connection with a memory. In some non-limiting embodiments, the parameter generator can be integrated into the imaging system 300 and/or the injection system 100.

The phase programming mechanism can, for example, allow the operator to control the injection system by entering a "protocol wizard or generation mode," "helper mode", or "operator assist mode." Once the operator chooses to enter the operator assist mode, the operator can be presented with a graphical user interface that provides a mechanism or mode for entering the information used in populating the phase parameters. In the operator assist mode, the protocol parameters are automatically populated, generally in response to information input by the operator through the graphical user interface and received at the parameter generator. The graphical user interface can present the operator with a series of choices, such as questions about the procedure, about the patient, or both, the answers to which can assist the software associated with the phase programming mechanism in determining the appropriate injection protocol and phase parameters.

Figure 2:
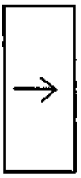
FIG. 2 illustrates an embodiment of a graphical interface from which an operator can choose a vascular region of interest for imaging.

For instance, one embodiment of a graphical user interface from which the operator is prompted to choose a region of interest for the image, and which follows the work flow described herein, is depicted in FIG. 2. The operator can, for example, choose a region of interest by highlighting, for example, using a touch screen or a mouse controlled cursor, a region of interest on an illustration of the body set forth on the user interface or can choose a region of interest from a menu such as a pull down menu. Hierarchical groupings of regions of interest can be provided.

Upon choosing the region to be imaged, the operator may be prompted to select from among different available preset protocols, each of which may have preset parameters associated therewith, such as the contrast concentration, whether a test injection or transit bolus are used, the maximum flow rate, the limitation on pressure, the injection duration, scan duration, etc., as shown in FIG. 2 and referred to therein as the "Details" of the protocol selected. The "Details" shown in FIG. 2 are exemplary only, and are not intended to be limiting. Preset protocol parameters may be stored in memory on the system, such as in memory associated with one or more of the above-described components of the system or in a database accessible over a network, and recalled when a particular protocol is selected. These preset values may have been entered into the system memory by an operator or someone associated therewith to reflect an operator's preferences for a particular protocol. These values may also have been pre-loaded into the system during programming, and may reflect values that are commonly used in the industry. Preset parameters such as "max flow rate" and "pressure limit" may be parameters that are set out of safety concerns for the patient. Others may be set as a function of the capabilities of the particular injector or scanner hardware of the system. In some embodiments, the preset values can be overridden, such as through direct entry of new values by an operator or through generation of a protocol requiring parameters inconsistent with the preset values. In the event that the preset values are inconsistent with a generated protocol, the operator may be prompted that such an event has occurred and given an opportunity to adjust and/or authorize the generated protocol.

Once a protocol is selected, the operator can then be prompted to enter values for other variables (for example, patient physiological variables such as the patient's weight, height, gender, etc., or procedure variables such as contrast concentration, tube voltage, scan duration, etc., though it should be understood that the general order in which the operator is prompted for information or in which the operator enters information is not intended to be limiting. FIG. 3 shows an exemplary graphical user interface wherein the variables "Patient Weight," "Concentration" and "Tube Voltage" are selected or entered. An example of an embodiment or implementation of this is to provide a keypad on the graphical user interface into which the operator enters the patient's weight in pounds or kilograms. In another embodiment, the operator chooses a weight range from among low, mid and high ranges. Similarly, the tube voltage can be entered using a keypad or selected from among several preset values. Such variables can also be measured by one or more sensing devices associated with the system and/or read electronically or digitally from patient records as may be kept in a hospital database accessible over a network. For example, the system can be configured to automatically populate the patient weight based on patient records or automatically populate the tube voltage based on the capabilities or current setting of the scanner of the associated imaging system. One or more of these variables may also be automatically populated based on one or more criteria selected in a previous step, such as the preset protocol selected in FIG. 2. The automatically populated value can then serve as the default unless and until changes are made thereto. The operator may also be queried if the operator wishes to perform a test injection or timing injection.

The location of the graphical user interface within the system is not intended to be limiting. In addition to an interface on the injector system, choices can also or alternatively be made on a graphical user interface on the imaging system or scanner and/or from a database on the imaging system or scanner. In the case that the choices are made via an interface or database resident on the scanner, the data can then be transmitted to the injector. Moreover, the interface can exist solely on the scanner/imaging system. In this case, the final protocol can be transmitted to the injection system. Likewise, the interface or database can exist on a machine or system separate from the injector and the scanner. Data, for example, protocols can be transmitted from that system to the injector. A communication interface that may be used herein is disclosed in U.S. Pat. No. 6,970,735, the contents of which is incorporated herein by reference. One or more imaging systems can also be connected by way of a network with a central control location where one or more computer interfaces can exist to display and/or allow for control of the networked imaging systems. For example, multiple imaging systems can be connected to a common computer or set of computers located in a control center, wherein an operator can monitor and adjust the protocols being used on one or more of the imaging systems. A radiologist wishing to specify the particular injection protocol to be used in a particular instance can take advantage of such a network to adjust the protocol from such an interface.

Figure 4:
FIG. 4 illustrates an embodiment of a graphical interface which presents an operator with a computed injection protocol.

Based upon the selections made, the software implementing the present invention computes an injection protocol, including parameters such as the flow rates and volumes for the phases, including the test injection, if any, for the operator's review. One such example of a graphical user interface displaying an injection protocol for the operator's review is shown in FIG. 4.

In certain non-limiting embodiments, computation of the parameters of the injection protocol is done using a variable weight factor (mg Iodine/Body weight kg) which is used to determine the dose, or total volume, of iodine for the patient for a particular tube voltage or range thereof. In general, there is a linear relation between the plasma concentration of iodine and the enhancement (or CT Number) in Hounsfield Units in a blood vessel. Weight is easily obtained before the patient is scanned and serves as a practical means of computing the preload volume of contrast. The requirement to compute a preload volume can be eliminated through use of a continuous flow system using bulk containers of, for example, contrast and a flushing fluid or diluent (for example, saline) as described, for example, in U.S. Pat. Nos. 6,901,283, 6,731,971, 6,442,418, 6,306,117, 6,149,627, 5,885,216, 5,843,037, and 5,806,519, U.S. Patent Application Publication No. 2006/0211989 (U.S. patent application Ser. No. 11/072,999), and International Patent Application Publication No. WO/2006/096388 (PCT International Patent Application No. PCT/US2006/007030), the contents of which are incorporated herein by reference.

In several embodiments, the process software discretizes the weight ranges of subjects in, for example, 7 ranges (for example, <40 kg, 40-59 kg, 60-74 kg, 75-94 kg, 95-109 kg, 110-125 kg, >125 kg) and the tube voltage in, for example, 4 values (80 kV$_p$, 100 kV$_p$, 120 kV$_p$ and 140 kV$_p$) for each weight range. Weight factors are associated with each weight range/tube voltage combination. Exemplary weight factors, which depend upon and vary with patient weights and tube voltages, are displayed in Table 2 below.

TABLE 2

Exemplary Weight Factors (gI/kg)

| Weight Bin | Weight Range (kg) | Weight Range (lbs) | 120 kV$_p$ |
|---|---|---|---|
| 1 | <40 | <88 | 0.5 |
| 2 | 40-59 | 88-131 | 0.46 |
| 3 | 60-74 | 132-163 | 0.38 |
| 4 | 75-94 | 164-208 | 0.34 |
| 5 | 95-109 | 209-241 | 0.33 |
| 6 | 110-125 | 242-276 | 0.31 |
| 7 | >125 | >276 | 0.3 |

The weight factors displayed in Table 2 were derived by applying a multi-objective optimization routine (Gembicki's weighted goal attainment method (Gembicki, F. W., "Vector Optimization for Control with Performance and Parameter Sensitivity Indices," Case Western Reserve University (1974)) to simulated patients representing each of the weight ranges. This process is outlined in United States Patent Application Publication Number 2010/0113887, assigned to the assignee of the present application, the entire contents of which are incorporated by reference.

A similar multi-objective optimization was run to determine the weight factor values for the same set of discretized weight ranges for tube voltages of 80, 100 and 140 $kV_p$. For each, a goal was set to attain an enhancement value of at least 325 HU in the right heart while keeping the contrast volumes and flow rates as low as possible. The weight factor values were calculated so as to provide the highest probability of meeting that goal. Other parameters were also considered in determining the weight factors. For example, the optimal value of the weight factor generally increases as the scan duration increases. This is primarily because more contrast is needed to ensure the enhancement target is met in the entire scan window. Moreover, longer scan durations typically imply lower flow rates, which can decrease enhancement and thus require additional contrast volume to compensate. However, the weight factors calculated can accommodate all scan duration values.

For each weight bin, the weight, height, age and gender were randomly generated for 50 simulated patients. The contrast dosing protocol parameters were varied during the simulation as follows:

Contrast Concentration: 320 and 370 mgI/mL
Scan Duration: 4, 10, 16 and 20 seconds
Minimum Injection Duration: 12 seconds
Max Flow Rate: 7 mL/s
Syringe Capacity: 194 mL
Dual Flow: ON and OFF The right heart compartment enhancement was calculated as the average enhancement during the scan window. A test bolus of 20 mL contrast, 40 mL saline was used to determine the appropriate timing for the scan window. The minimum injection duration was not varied because it is usually set at 12 seconds when performing an injection for cardiac imaging. It is not generally necessary to vary the minimum injection duration value as long as the scan duration values are chosen so as to simulate all possible states of volume and flow rate adjustment during protocol generation.

For each of the simulated patients, all possible permutations of the above parameters were simulated according to the PK model described by Bae. K. T. Bae, J. P. Heiken, and J. A. Brink, "Aortic and hepatic contrast medium enhancement at CT. Part I. Prediction with a computer model," Radiology, vol. 207, pp. 647-55 (1998); K. T. Bae, "Peak contrast enhancement in CT and MR angiography: when does it occur and why? Pharmacokinetic study in a porcine model," Radiology, vol. 227, pp. 809-16 (2003); K. T. Bae et al., "Multiphasic Injection. Method for Uniform Prolonged Vascular Enhancement at CT Angiography: Pharmacokinetic Analysis and Experimental Porcine Method," Radiology, vol. 216, pp. 872-880 (2000); U.S. Pat. Nos. 5,583,902, 5,687,208, 6,055,985, 6,470,889 and 6,635,030.

In choosing the best possible weight factor values, a set of enhancement criteria were defined for each application. For pulmonary angiography, for example, the set goal was to achieve at least 325 HU of enhancement while using the least possible contrast and the lowest flow rate. A cost function was constructed according to the following equation:

$$\text{Cost}=0.7\times|E_{RH}-325|+0.2\times(R-5)+0.1\times V_{cD} \qquad (1)$$

R: flow rate (mL/s)
$V_{cD}$: contrast diagnostic volume (mL)
$E_{RH}$: Mean enhancement in right heart during scan window (HU)

In addition, it was considered desirable to restrict the number of cases where the right heart enhancement fell below 275 HU. Thus, for each weight bin, the statistical distribution of weight factor values for all cases meeting a cost function target of 47.5, which was an arbitrarily selected cost function target based on what was understood to be an acceptable value, was compared to the distribution of weight factor values for which the enhancement in the right heart was less than 275 HU and another distribution for cases not meeting the cost function target where the flow rate exceeded 6 mL/s.

Figure 5:
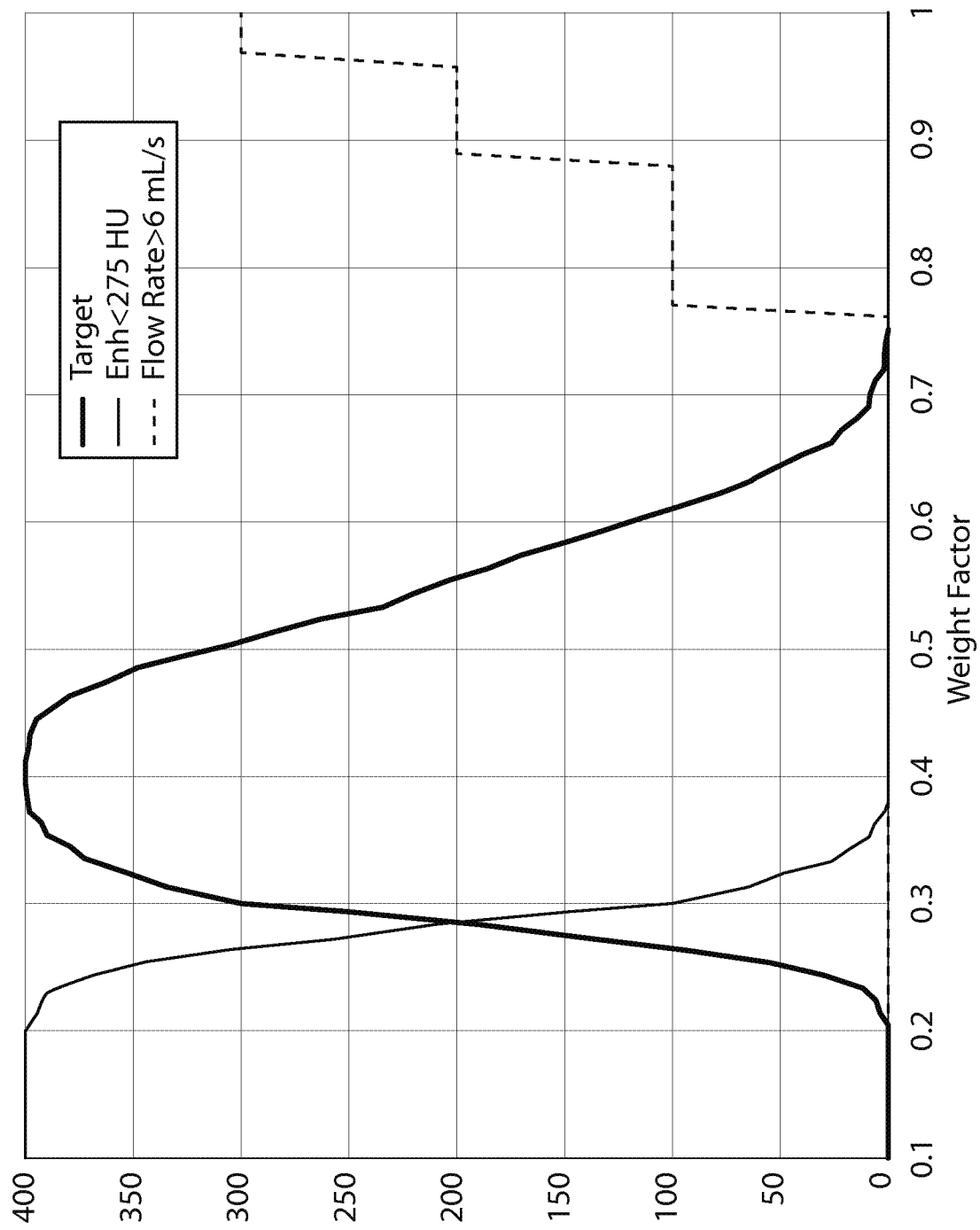
FIG. 5 illustrates a simulated histogram in the right heart compartment.

The histograms of each distribution were computed, and the point where the maximum positive difference between the high and low enhancement distributions was observed was considered to be the best possible weight factor value as it represents the value where the enhancement criteria will be met most of the time and where the enhancement in the right heart will only fall below 300 HU in a very limited number of cases. FIG. 5 shows an example of the histogram distribution for a tube voltage of 100 $kV_p$ and a weight bin of 40-59 kg.

From the histogram shown in FIG. 5, a weight factor of 0.39 gI/kg was considered optimal for the subject weight range/tube voltage combination. Less than 1% of low enhancement cases occurred at this value according to the simulation. A cumulative distribution function would show that no cases of low enhancement or high flow rate occur for weight factors greater than or equal to 0.4 gI/kg. Thus, choosing the point of largest positive difference also ensures there is very little overlap between the two distribution curves.

The simulations described above were used to determine if patient or injection protocol parameters are likely to influence the enhancement outcomes, or, in other words, to determine whether it is more likely to achieve the specified enhancement target for either a given type of patient or a specific injection protocol. To analyze the effect of patient age, for example, the average age of simulated patients who met the 325 HU target was compared to the average age of the entire simulated patient population. This was done for each value of the tube voltage and across all weight bins. The results are shown in Table 3, below.

TABLE 3

Influence of Patient Age

| Category | Average Age (yrs) | Std. Dev. | Age Range (yrs) | p-value |
| --- | --- | --- | --- | --- |
| All patients | 42.7 | 20.15 | 10-86 | — |
| Target Met at 80 $kV_p$ | 47.36 | 19.36 | 10-86 | $9 \times 10^{-4}$ |
| Target Met at 100 $kV_p$ | 47.36 | 19.36 | 10-86 | $9 \times 10^{-4}$ |
| Target Met at 120 $kV_p$ | 48.1 | 19.21 | 10-86 | |
| Target Met at 140 $kV_p$ | 49.9 | 19.52 | 10-86 | $1.55 \times 10^{-6}$ |

The results of Table 3 show that the average age of patients in cases where the enhancement target is met is statistically significantly different from the average age of the overall patient population, demonstrating a slight tilt towards older patients. A likely explanation for this is that, generally speaking, older patients tend to exhibit lower cardiac output values, which leads to higher enhancement peaks.

The height of the simulated patients was also evaluated in a similar way, and the results of this evaluation are shown in Table 4, below.

TABLE 4

Influence of Patient Height

| Category | Average Height (in) | Std. Dev. | Height Range (in) | p-value |
|---|---|---|---|---|
| All patients | 67.52 | 7 | 48-79 | — |
| Target Met at 80 $kV_p$ | 65.77 | 7.6 | 48-79 | 0 |
| Target Met at 100 $kV_p$ | 67.56 | 7.64 | 48-79 | $8.59 \times 10^{-7}$ |
| Target Met at 120 $kV_p$ | 66.4 | 7.1 | 48-79 | 0 |
| Target Met at 140 $kV_p$ | 66.41 | 6.9 | 48-79 | 0 |

From the results shown in Table 4, it is evident that the differences in height between the groups where the enhancement target is met and the general patient population are not significant. The difference achieves statistical significance, but in physical terms has no practical meaning.

The influence of scan duration was also measured, which was observed by calculating for each tube voltage value the percentage of scans which successfully met the target obtained for each of the four scan duration values. The results of this evaluation are shown in Table 5.

TABLE 5

Percentage of success for different scan durations

| Tube Voltage | 4 sec | 10 sec | 16 sec | 20 sec |
|---|---|---|---|---|
| 80 $kV_p$ | 24% | 23% | 25% | 28% |
| 100 $kV_p$ | 32% | 22% | 23% | 23% |
| 120 $kV_p$ | 36% | 25% | 20% | 19% |
| 140 $kV_p$ | 40% | 27% | 17% | 16% |

In Table 5, the proportion of successful cases occurring for scan durations of 4 and 10 seconds tends to increase as the tube voltage increases while it decreases for scan durations of 16 and 20 seconds. This is likely, at least in part, because for longer scan durations, the average enhancement is lower due to both a longer scan window and a slower contrast injection rate. As the tube voltage increases, the amount of contrast required to attain the enhancement target increases as well. This can lead to instances where the amount of contrast calculated by the protocol exceeds the syringe capacity, leading to a lower than expected enhancement plateau in the scan window. When this occurs, the shorter scan duration windows are more likely to meet the enhancement target since the scan will only occur during the period of highest enhancement.

The influence of contrast concentration and gender were also evaluated, and the results of this evaluation are shown in Tables 6 and 7, below.

TABLE 6

Percentage of success for contrast concentration

| Tube Voltage | 320 mgI/mL | 370 mgI/mL |
|---|---|---|
| 80 $kV_p$ | 48% | 52% |
| 100 $kV_p$ | 55% | 45% |
| 120 $kV_p$ | 50% | 50% |
| 140 $kV_p$ | 47% | 53% |

TABLE 7

Percentage of success for gender

| Tube Voltage | Male | Female |
|---|---|---|
| 80 $kV_p$ | 52% | 48% |
| 100 $kV_p$ | 51% | 49% |
| 120 $kV_p$ | 49% | 51% |
| 140 $kV_p$ | 45% | 55% |

From the data in Table 6, it does not appear that contrast concentration has a particular influence on the incidence of success as both tested contrast concentrations led to similar percentages of successful outcomes. Similarly, from Table 7, it does not appear that gender has any particular influence on successfully achieving enhancement targets.

The above simulations were used to develop the weight factors of Table 8, below.

TABLE 8

Exemplary Weight Factors (gI/kg)

| Weight Bin | Weight Range (kg) | Weight Range (lbs) | 80 $kV_p$ | 100 $kV_p$ | 120 $kV_p$ | 140 $kV_p$ |
|---|---|---|---|---|---|---|
| 1 | <40 | <88 | 0.36 | 0.44 | 0.5 | 0.59 |
| 2 | 40-59 | 88-131 | 0.33 | 0.39 | 0.46 | 0.51 |
| 3 | 60-74 | 132-163 | 0.28 | 0.33 | 0.38 | 0.44 |
| 4 | 75-94 | 164-208 | 0.26 | 0.31 | 0.34 | 0.4 |
| 5 | 95-109 | 209-241 | 0.24 | 0.29 | 0.33 | 0.39 |
| 6 | 110-125 | 242-276 | 0.23 | 0.27 | 0.31 | 0.37 |
| 7 | >125 | >276 | 0.23 | 0.27 | 0.3 | 0.35 |

Additionally, the weight factors in Table 8 were verified to ensure that they do not yield unrealistic injection protocols. To do so, statistical analysis of the flow rate and contrast volume usage was performed to verify that injection protocols generated according to the procedure outlined in U.S. Patent Application Publication No. 2010/0113887 using these weight factors were feasible. The results of this analysis are shown in FIGS. 6-8 and described below.

Figure 6:
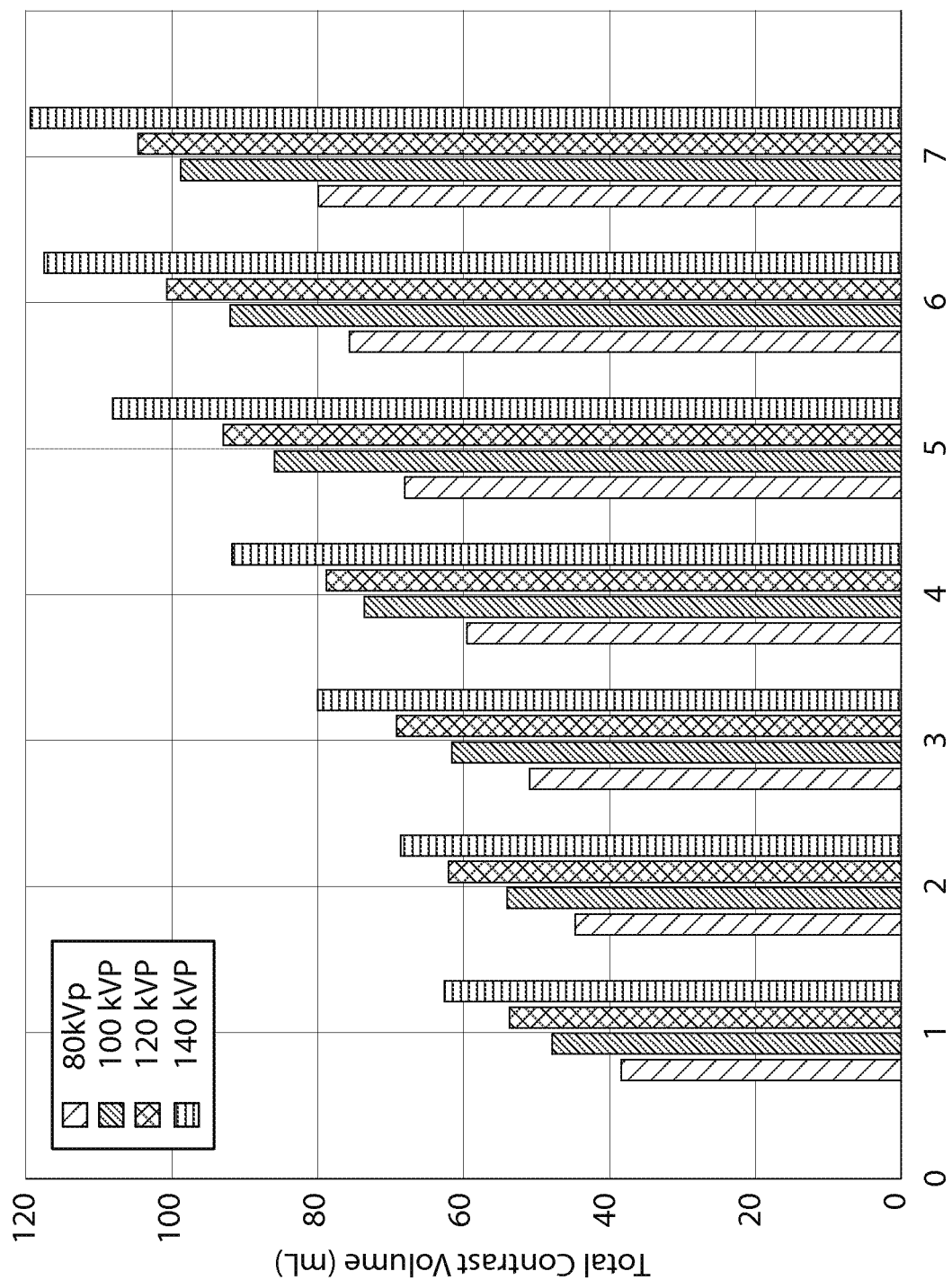
FIG. 6 illustrates the total contrast material delivered to simulated patients for different weight values and tube voltage values according to contrast delivery protocols generated using an embodiment of a parameter generation system.

FIG. 6 shows that contrast volumes calculated with the weight factor values of Table 8 will not yield unrealistic protocols in terms of total volume of contrast delivered. As shown, the average volume increased with tube voltage and with weight bin, as expected. The smallest volume of contrast calculated at 80 $kV_p$ was 29.2 mL, while the largest volume of contrast calculated at 140 $kV_p$ was 161 mL. This is the range of volumes calculated by the protocol algorithms of U.S. Patent Application Publication No. 2010/0113887 using the weight factors of Table 8.

Figure 7:
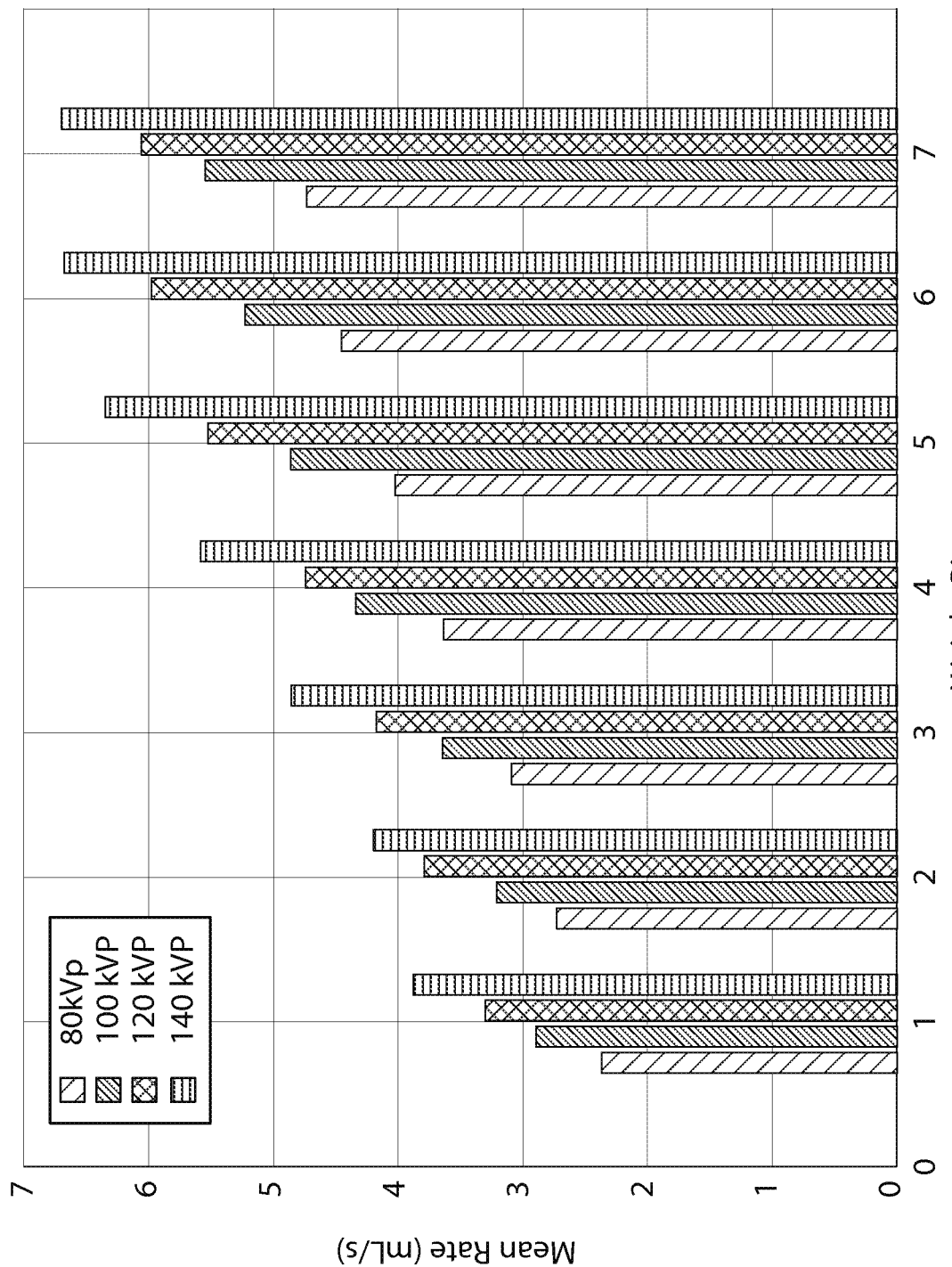
FIG. 7 illustrates the mean flow rate of contrast material delivered to simulated patients for different weight values and tube voltage values according to contrast delivery protocols generated using an embodiment of a parameter generation system.

In FIG. 7, the flow rates calculated by the algorithm using the weight factors of Table 8 also increased with tube voltage and weight bin. The values calculated are all realistic and are all capable of being used in injection protocols in a clinical setting. The slowest rate used in the sampling at 80 $kV_p$ was 2 mL/s and the fastest rate used at 140 $kV_p$ was 7 mL/s, due to flow rate limitations.

Figure 8:
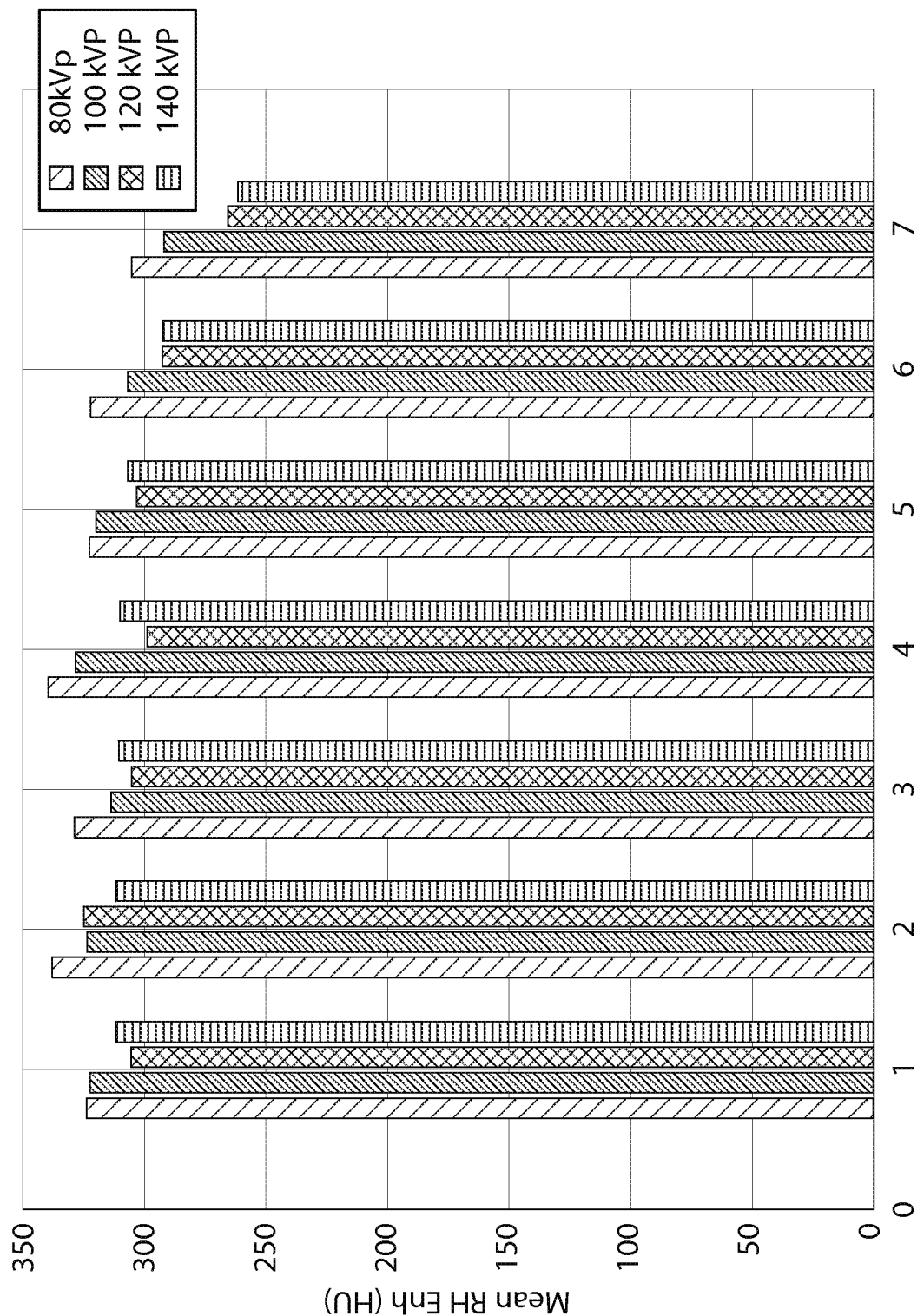
FIG. 8 illustrates the mean right heart (RH) enhancement value achieved in simulated patients for different weight values and tube voltage values according to contrast delivery protocols generated using an embodiment of a parameter generation system.

The mean right heart enhancement across the scan window was also calculated using the weight factors of Table 8 and the results are displayed in FIG. 8. For most weight bins, the enhancement target of 325 HU was easily met when the tube voltage was set to either 80 $kV_p$ or 100 $kV_p$. For 120 $kV_p$ and 140 $kV_p$ settings, the enhancement target was not met as often, in part because for these values, syringe capacity can be a limiting factor and cause an injection protocol to get truncated. Moreover, at 120 $kV_p$, the weight factors were set at or below the original weight factor values in an effort to limit the flow rates and volumes for pulmonary angiography applications.

Clinical testing of the weight factors of Table 8 was also conducted using patient data from clinical trials at UPMC and Muenster. In the testing, there were 105 patients, whose summary statistics are presented in Table 9 below.

TABLE 9

Test Set Data Statistics

|  | Mean | Standard Deviation | Range |
| --- | --- | --- | --- |
| Weight (lbs) | 180.12 | 44.9 | 90-450 |
| Height (inches) | 68.3 | 3.86 | 59-78 |
| Age (years) | 50.8 | 18.07 | 19-89 |

Figure 9:
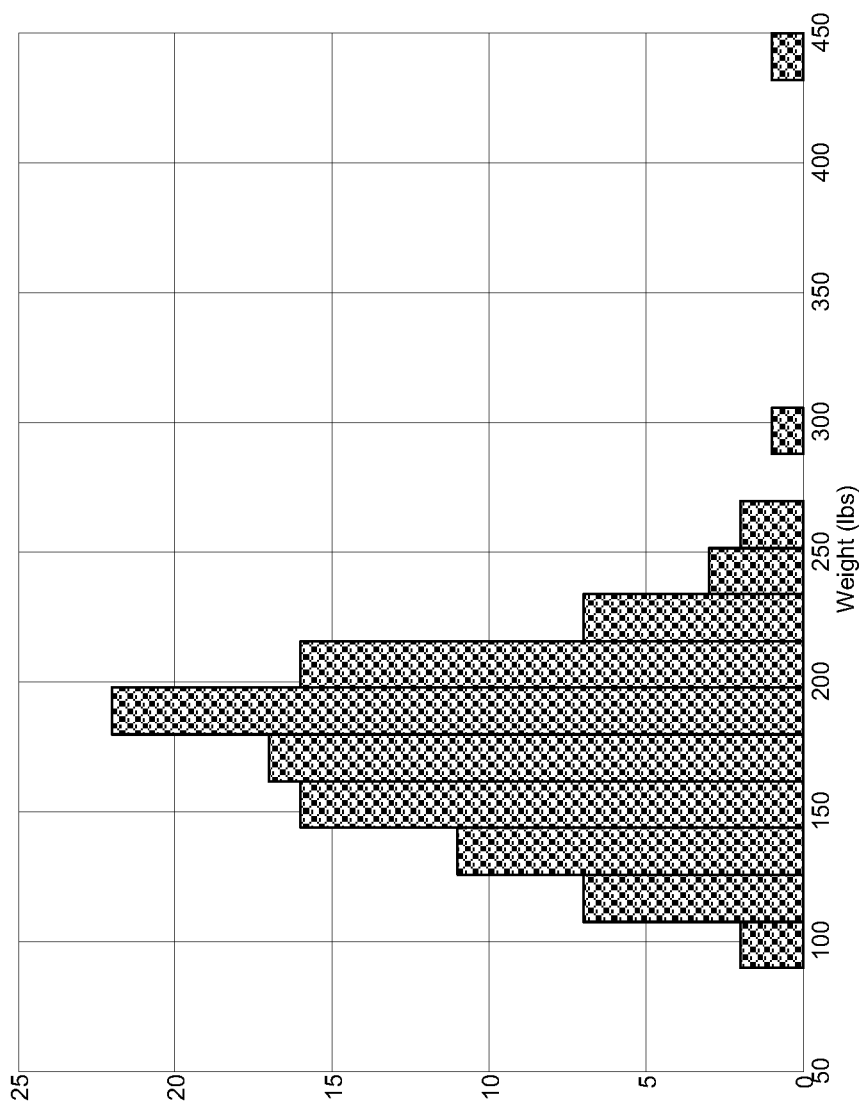
FIG. 9 illustrates the distribution of patient weight of a patient sampling.
Figure 10:
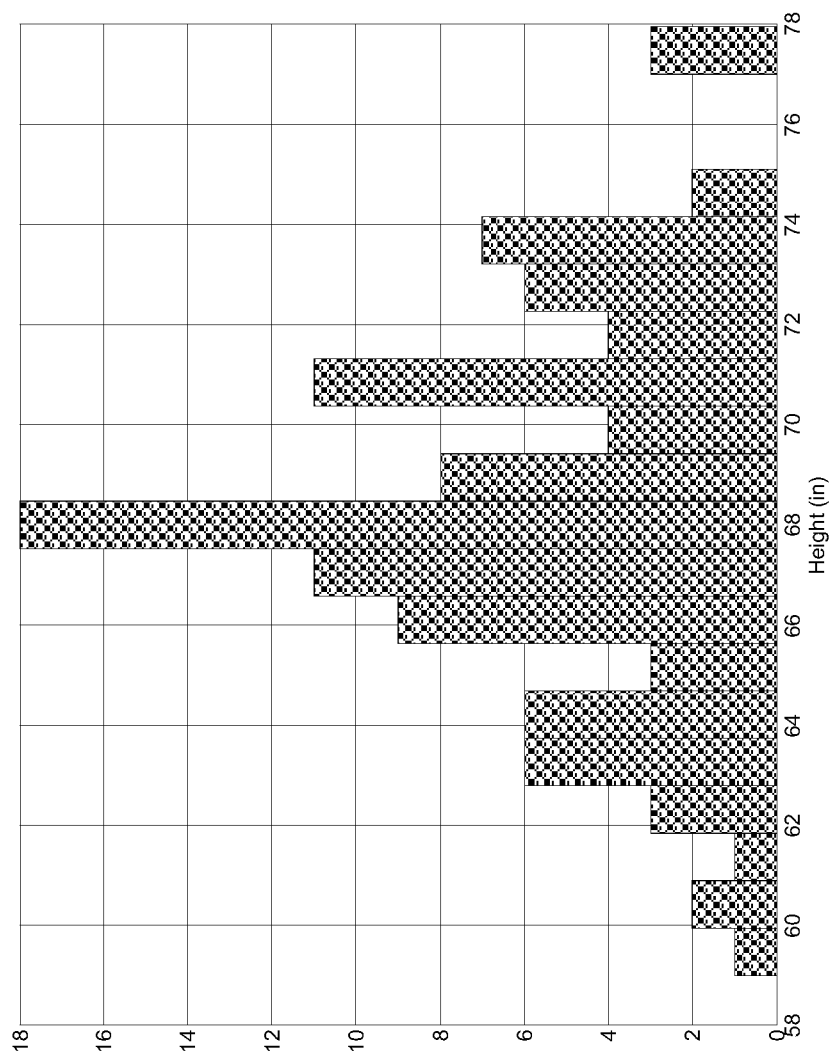
FIG. 10 illustrates the distribution of patient height of the patient sampling of FIG. 9.
Figure 11:
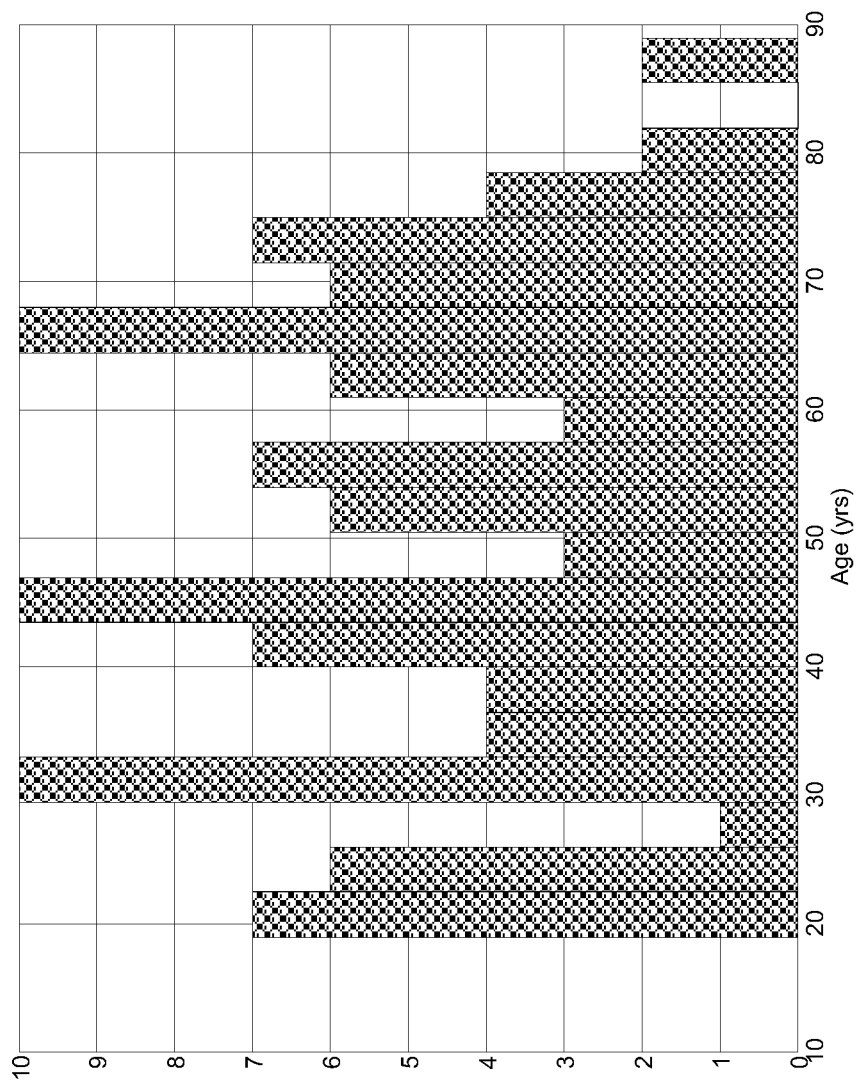
FIG. 11 illustrates the distribution of patient age of the patient sampling of FIG. 9.

The sampling included 63 male patients and 42 female patients. FIGS. 9, 10, and 11 represent the weight, height and age distribution of the sampling, respectively.

Figure 12:
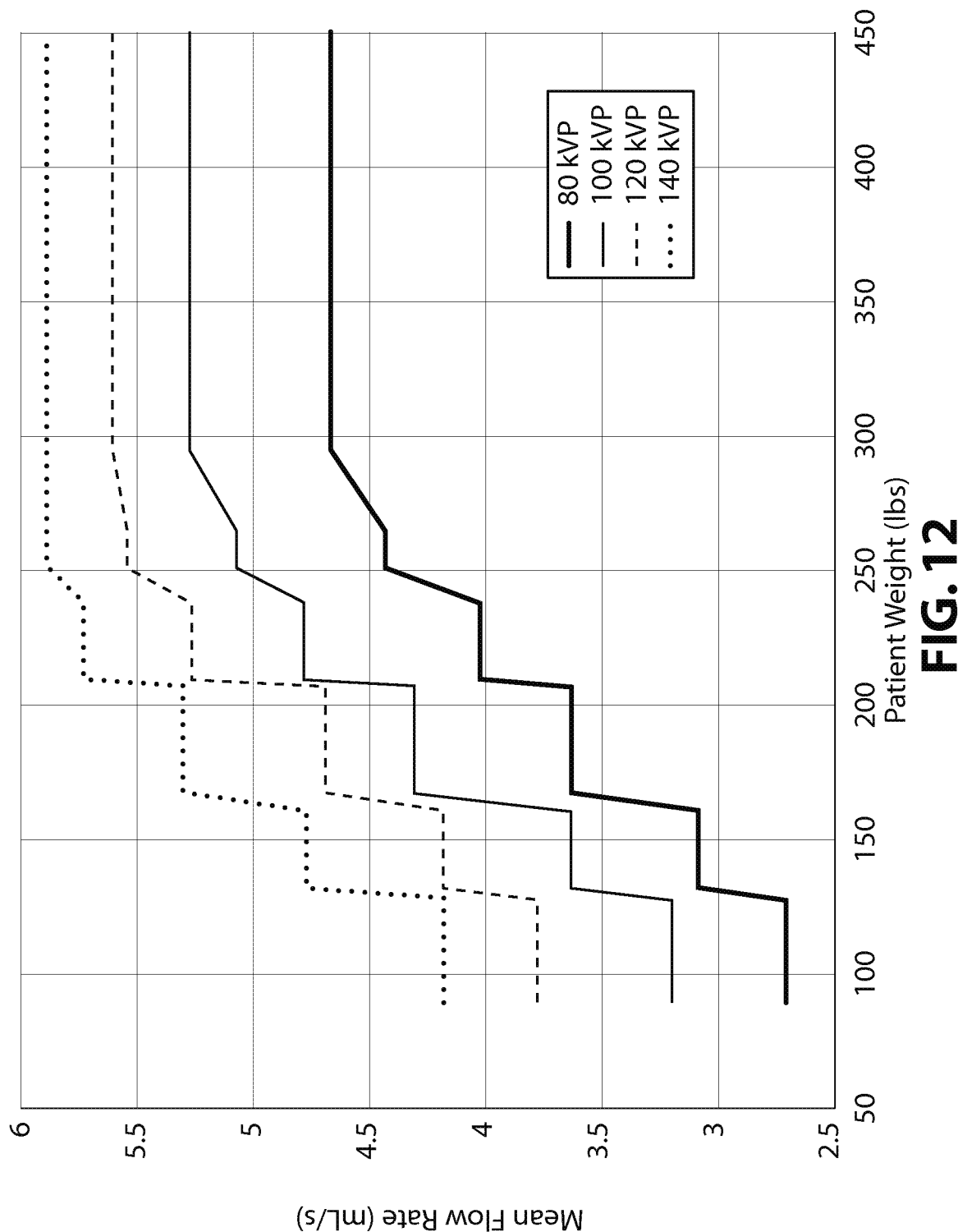
FIG. 12 illustrates the average flow rate at different patient weights for the patient sampling of FIG. 9 according to contrast delivery protocols generated at different tube voltages using an embodiment of a parameter generation system.

The simulation described above was run on this patient data using the weight factors of Table 8. For each patient weight, an injection protocol was calculated according to the protocol calculation process outlined in U.S. Patent Application Publication No. 2010/0113887 for each tube voltage and the average flow rate of each of the injection protocols was plotted against patient weights for each tube voltage value. The results are shown in FIG. 12. In these results, the flow rates increased as the tube voltage value increased, but the average value of the flow rates stayed inferior to 6 mL/s, even for the highest tube voltage setting. The flow rates obtained for the calculated injection protocols were thus within the expected range.

Figure 13:
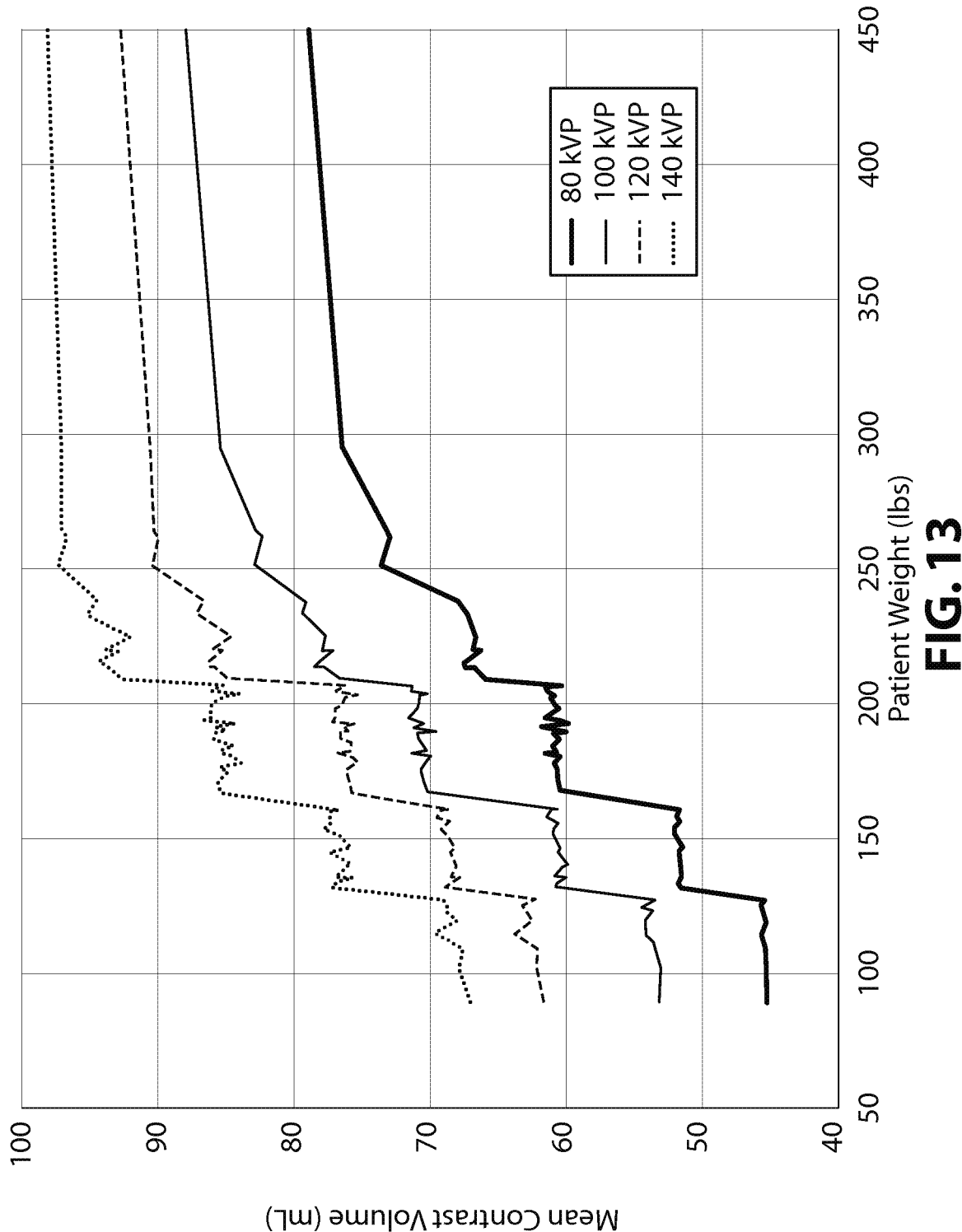
FIG. 13 illustrates the mean total contrast volume delivered at different patient weights for the patient sampling of FIG. 9 according to contrast delivery protocols generated at different tube voltages using an embodiment of a parameter generation system.

Similarly, the total contrast volume used in the injection protocol, including in the diagnostic phase and the dual flow phase, was also calculated for each patient and plotted against weight, the results of which are shown in FIG. 13. In FIG. 13, the average volume stayed under 100 mL for all injection protocols. There were, however, cases where the volume exceeded 100 mL, particularly for the heavier patients.

Figure 14:
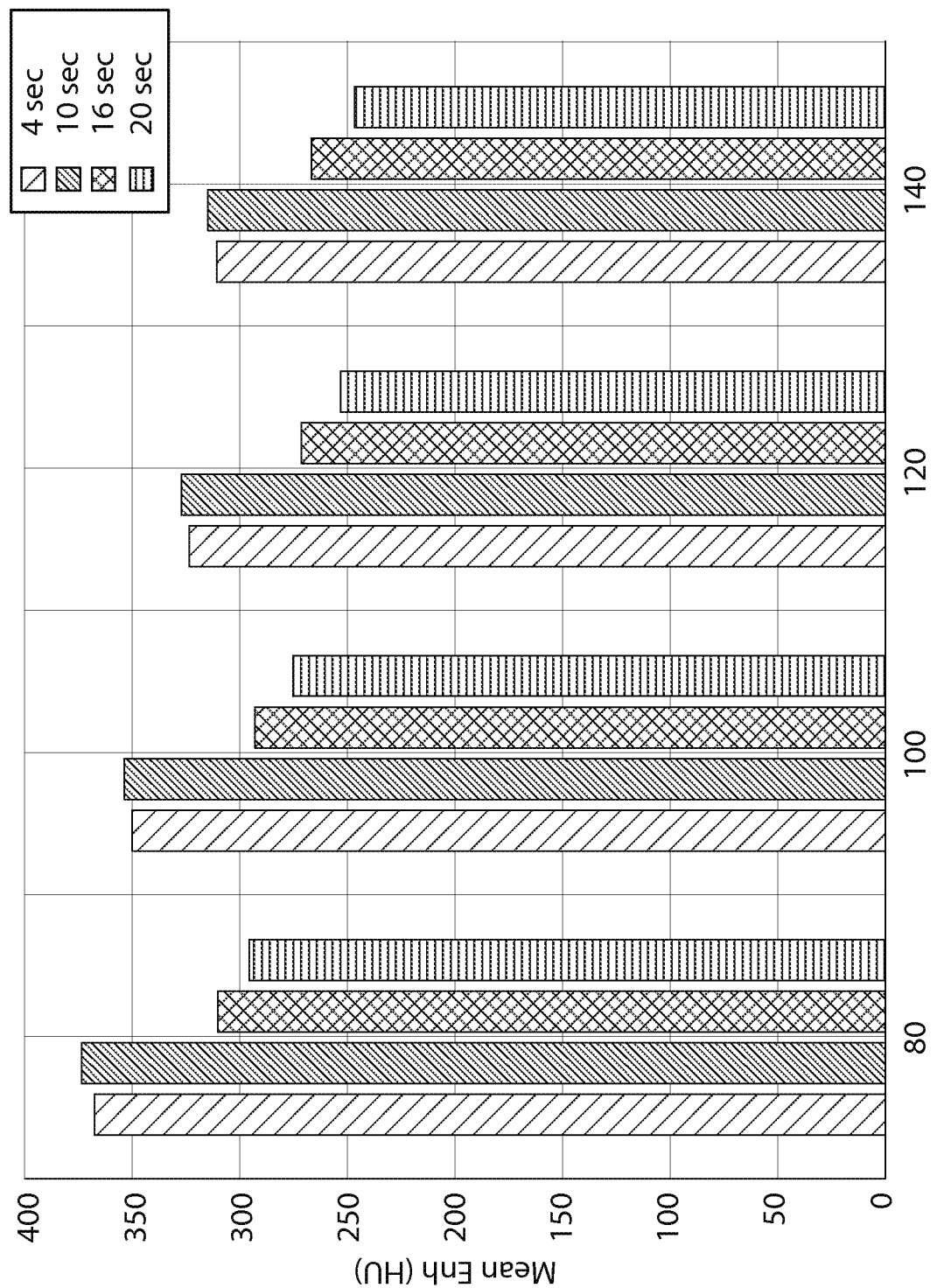
FIG. 14 illustrates the mean enhancement value in the patient sampling of FIG. 9 for different scan durations according to contrast delivery protocols generated at different tube voltage values using an embodiment of a parameter generation system.
Figure 15:
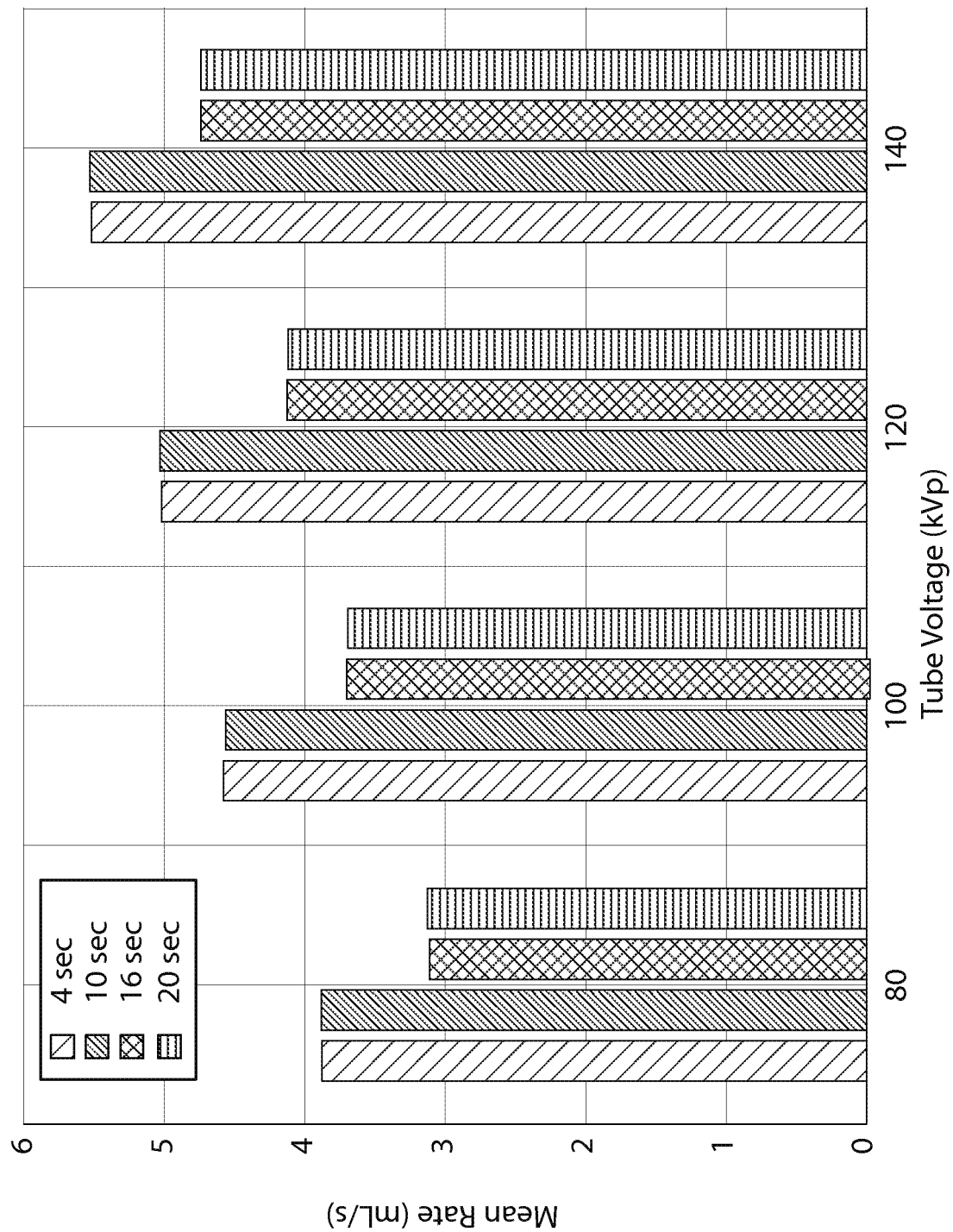
FIG. 15 illustrates the mean flow rate of contrast volume delivered at different scan durations for the patient sampling of FIG. 9 according to contrast delivery protocols generated at different tube voltage values using an embodiment of a parameter generation system.

FIG. 14 reflects the effect of scan duration on the right heart enhancement value in the patient sampling. FIG. 14 shows that the enhancement value is lower for 16 and 20 second scan durations than for 4 and 10 second scan durations. This is believed to be due, at least in part, to the fact that the enhancement value was calculated as the average enhancement value in the scan window, thus causing longer scan windows to have lower average enhancement values. Moreover, as shown in FIG. 15, shorter scan durations typically result in higher flow rates, further contributing to an increase in the enhancement value. However, if the scan duration is shorter than the minimum injection duration tested of 4 seconds, the diagnostic phase contrast volume is reduced, which explains why the enhancement tends to be lower for 4 second scan durations than for 10 second scan durations. The enhancement also tended to dip below 300 HU for scan durations above 16 seconds in FIG. 14.

Figure 16:
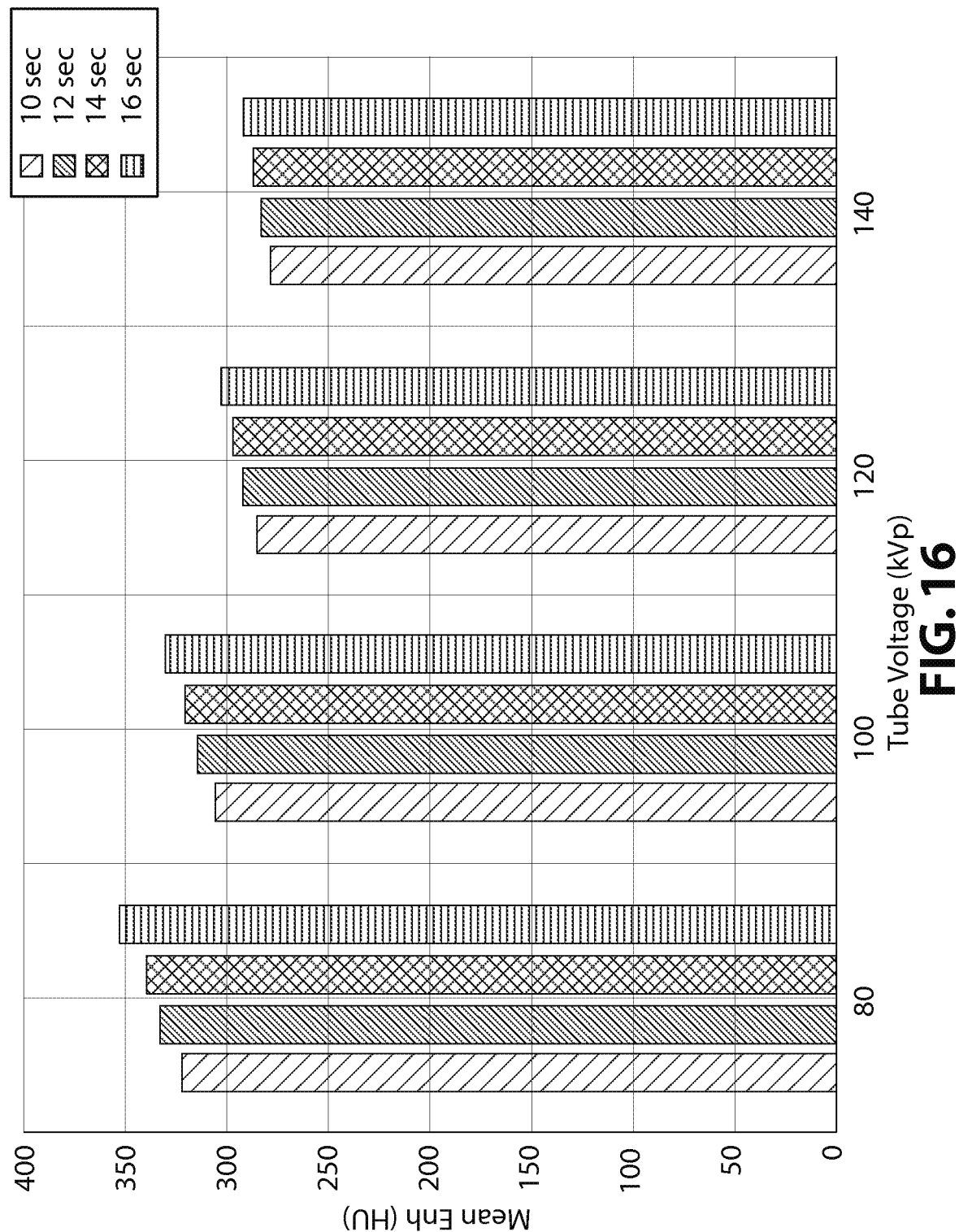
FIG. 16 illustrates the mean enhancement value in the patient sampling of FIG. 9 at different injection durations according to contrast delivery protocols generated at different tube voltage values using an embodiment of a parameter generation system.

FIG. 16 shows the effect of the minimum injection duration on the mean enhancement value. In particular, for the patient sampling plotted in FIG. 16, the average enhancement in the right heart falls below 300 HU for tube voltage values of 120 $kV_p$ and 140 $kV_p$, but remains above this threshold for the lower tube voltage values, regardless of the scan duration programmed.

Using the weight factors, injection protocols for a patient can be determined by the system according to a weight-based algorithm. One such embodiment of a weight-based algorithm for determining a volume of a pharmaceutical fluid, such as contrast, that is to be injected during an injection phase is represented by the following equation:

$$V_1 = \text{patient weight} * X * Y \quad (2)$$

$V_1$: volume of pharmaceutical fluid to be delivered in the phase;

X: weight factor;

Y: contrast concentration in pharmaceutical fluid

Once the total volume to be delivered during a particular phase is known, the system can determine the appropriate flow rate for a particular phase according to the formula:

$$\text{Flow Rate} = V_1/\text{injection duration} \quad (3)$$

The injection duration can be determined in a variety of ways. For example, the injection duration can be determined by the system based upon one or more criteria concerning the imaging procedure (e.g., the region of the body to be imaged) and/or the patient (e.g. patient weight), it can be a value that is inputted directly by the operator, or it can represent a preset parameter, as described above.

Parameters of additional phases can be similarly determined. For example, the system can determine parameters for a first phase in which only the pharmaceutical fluid is to be delivered and a second, diluted phase in which both the pharmaceutical fluid and a diluent, such as saline, are to be delivered.

The implementation software can be programmed to generate parameters of the injection protocol based on the above algorithms and weight factors, which are based, in part, on the x-ray tube voltage. Once generated, the parameters can be populated in the graphical user interface for operator review. As described previously, FIG. 4 represents an embodiment of a graphical user interface capable of presenting an injection protocol to the operator for review. In different embodiments, the weight factors can be determined by the system through an algorithmic approach whereby the weight factors are calculated using information about patient weight, tube voltage, etc., such as is described above. The weight factors can alternatively, or additionally, preexist in memory, such as in a lookup table data file loaded onto the system or accessible by the system across a network, allowing the weight factors to be recalled when needed. Table 8, for example, illustrates exemplary information concerning the weight factors that could be made available in a lookup table.

In other non-limiting embodiments, determination of appropriate injection protocol parameters can be accomplished by modifying or adjusting protocol parameters of a baseline injection protocol using a tube voltage modification factor to account for differences between the voltage being applied to an x-ray tube during a particular scan (or phase thereof) and the tube voltage that was used or assumed in determining the parameters of the baseline protocol.

For purposes of this disclosure, baseline injection protocols include protocols that have been established in the clinical literature, established through the collection of patient data over time by, for example, employing artificial intelligence techniques, statistical means, adaptive learning methodologies, etc., or established through mathematical modeling. These protocols may depend on, for example, contrast agent concentration, for example, iodine concentration in the case of a CT procedure, a patient parameter, for example, body weight, height, gender, age, cardiac output, etc., the type of scan being performed, the type of catheter inserted into the patient for intravascular access, and/or other patient specific data. In some non-limiting examples, baseline protocols have been, or can be, generated using a weight factor similar to the generation of protocols using weight factors discussed above. Such protocols, as well as methods and systems for generating such protocols, are described in PCT International Patent Application No. PCT/US05/41913, entitled MODELING OF PHARMACEUTICAL PROPAGATION, filed Nov. 16, 2005, claiming the benefit of U.S. Provisional Patent Application Ser. No. 60/628,201, assigned to the assignee of the present invention, and PCT International Patent Application No. PCT/US07/26194, entitled PATIENT-BASED PARAMETER GENERATION SYSTEMS FOR MEDICAL INJECTION PROCEDURES, filed Dec. 21, 2007, claiming the benefit of U.S. Provisional Patent Application Ser. Nos. 60/877,779 and 60/976,002, assigned to the assignee of the present invention, the disclosures of which are incorporated herein by reference.

Baseline injection protocols for use herein may be stored in memory on the system, made accessible to the system across a network, or determined by the system in response to one or more inputted values. For example, a series of baseline injection protocols, each known to provide optimal dosing parameters for a certain combination of scan region, body weight, contrast concentration, etc. at a particular tube voltage may be stored in memory. The system can then recall from memory information about the appropriate baseline protocol for use in generating an injection protocol once sufficient information about the to-be-generated injection protocol is known. For example, when an operator selects a scan region/body weight/contrast concentration combination for a new injection procedure, the system can recall a baseline protocol generated for the same, or a similar, combination of scan region/body weight/contrast concentration. Alternatively, the system may contain software which can compute baseline injection protocols based on one or more patient-specific or procedure-specific criteria inputted by the operator, including the values discussed above (e.g., patient-specific and procedure-specific parameters).

Baseline injection protocols generally reflect optimal contrast dosing parameters at a particular tube voltage, which is referred to herein as the baseline tube voltage. The most common baseline tube voltage is 120 $kV_p$. The baseline tube voltage associated with a baseline injection protocol can be stored along with other information about the baseline injection protocol, though in some non-limiting embodiments the operator may be prompted to enter the baseline tube voltage for a particular baseline injection protocol or the baseline tube voltage may be assumed to be 120 $kV_p$. Because of the relationship between tube voltage and attenuation, a baseline injection protocol may not provide optimal contrast dosing parameters if a tube voltage other than the baseline tube voltage is being applied when using that protocol. Accordingly, the baseline protocol parameters can be modified or adjusted in order to achieve more optimal contrast dosing at the new tube voltage value. Since the modified parameters are not readily known to the operator of the injector, the parameter generation system described herein eases the task of an operator by providing tube voltage modification factors that should be used in conjunction with a baseline injection protocol to determine more optimum injection parameters for the tube voltage of interest.

In several non-limiting embodiments, applying a tube voltage modification factor to one or more of the parameters of a baseline injection protocol may be used to create a new injection protocol tailored for the particular tube voltage to be used in the scan, such as by adjusting or modifying the parameters of the baseline protocol.

In one non-limiting embodiment, the tube voltage modification factors are determined from an analysis of the relationship between the attenuation to contrast concentration ratios (k-factor) and tube voltage. The relationship between the k-factor and tube voltage can be established through a review of the clinical literature, and an art recognized relationship is shown in Table 1 above. Alternatively, or additionally, the relationship between the k-factor and the tube voltage can be determined by performing a calibration exercise at the scanner.

One such calibration exercise involves preparing a number of vials, each containing a mix of a known iodine concentration, typically in mgI/mL. The vials are then scanned at different tube voltages, such as at 80, 100, 120, and 140 $kV_p$, and the attenuation value for each vial at each tube voltage is recorded. The tube voltages tested should at least include the baseline tube voltage used in determining the baseline protocol, which is typically 120 $kV_p$, as well as any other tube voltages that may be used with the scanner, the reason for which will become apparent below. For each of the tube voltages tested, the vial concentrations are plotted against the recorded attenuation values and a best-fit line is prepared for each tube voltage. For each tube voltage, the slope of the best-fit line represents the respective k-factor for that particular tube voltage, in units of HU/mgI/mL. Typical k-factor values determined according to this calibration exercise should generally correspond to those art recognized values reported in Table 1.

The tube voltage modification factors for different tube voltages can be determined based on the k-factors and information about the baseline tube voltage by calculating the relative increase or decrease in the k-factor between a particular tube voltage and the baseline tube voltage. For example, if the baseline tube voltage has a k-factor of 25 HU/mgI/mL, the tube voltage modification factor corresponding to a tube voltage having a k-factor of 41 HU/mgI/mL would be calculated as (25-41)/41, or -39%.

Table 10 below illustrates tube voltage modification factors for different tube voltages assuming the baseline tube voltage is 120 $kV_p$, using the k-factors from Table 1.

TABLE 10

Sample Tube Voltage Modification Factor Calculation

| Tube Voltage ($kV_p$) | k-Factor (HU/mgI/ml) | Modification Factor |
|---|---|---|
| 80 | 41 | (25 − 41)/41 = −39% |
| 100 | 31 | (25 − 31)/31 = −19% |
| 120 | 25 | (25 − 25)/25 = 0% |
| 140 | 21 | (25 − 21)/21 = +19% |

Additional adjustment of the calculated tube voltage modification factors may be appropriate at the operator's discretion, as other aspects of the image, noise in particular, change with tube voltage modifications. Therefore, an operator may prefer that instead of a 39% decrease at 80 $kV_p$, for example, only a 30% decrease be used. While the default computed values are suggested by the software based on the calibration experiment results, the operator would be able to modify the suggested values at his or her preference.

Once the tube voltage modification factors are known, the operator may decide which parameters of the baseline injection protocol should be adjusted based on the modification factors. For example, the operator may decide that both the total volume and flow rate parameters should be adjusted based on the tube voltage modification factor in order to maintain a constant injection duration, or only the total volume may be decreased in order to maintain a constant flow rate and decrease the injection duration. Typically, if the flow rate of contrast is modified, the flow rates of any saline phases are adjusted by the same amount to maintain consistency between the diagnostic contrast phases, the saline patency checks, and the saline flushes. Alternatively, the software can be set to automatically select one or more parameters of the baseline injection protocol to adjust according to the tube voltage modification factor, typically the volume and flow rate.

The parameter generator must also know or be able to identify the tube voltage to be applied as part of the new injection procedure in order to determine the appropriate tube voltage modification factor to apply. For example, the value of the tube voltage can be inputted by the operator directly to the parameter generator or the parameter generator can receive information about the tube voltage from the scanner or another component of the system, wherein the tube voltage is known to the component because of a particular setting or capability of the component or because an operator has input the tube voltage value to the component. Once known, an injection protocol can be generated by applying the tube voltage modification factor to the baseline protocol parameters. For example, in the case of modifying the volume and flow rate of the baseline protocol, generation of new volume and flow rate parameters involves increasing or decreasing the volume and flow rate parameters of the baseline protocol by the tube voltage modification factor. Generation of the injection protocols can be accomplished by the software of the system by recalling from memory and/or generating a baseline protocol, determining a tube voltage modification factor based on the details of the baseline protocol selected, including the baseline tube voltage and the intended tube voltage to be applied, and adjusting the baseline protocol parameters by the tube voltage modification factor.

Adjustment of the protocol parameters using the tube voltage modification factor allows for a baseline protocol to be modified in order to maintain similar enhancement characteristics despite a change in the tube voltage. For example, if a given volume and flow rate provide 300 HU of enhancement in a given region of interest scanned at 120 $kV_p$, the iodine concentration in that region can be calculated from the k-factor in Table 1 to be 12 mgI/mL (300 HU÷25 HU/mgI/ml). Using the same volume and flow rate (and thus assuming the same iodine concentration in that region) to scan the same region of interest at 100 $kV_p$ would be expected to provide 372 HU of enhancement using the k-factor in Table 1 (31 HU/mgI/mL*12 mgI/mL). To maintain the 300 HU at 100 $kV_p$, the volume and/or flow rate can be decreased by the tube voltage modification factor of 19% to obtain an iodine concentration of 9.7 mgI/mL.

Similar to the embodiments described above, an operator can be presented with a graphical user interface that provides a mechanism or mode for entering the information necessary for populating the phase parameters based on a tube voltage modification factor.

For instance, one embodiment of a graphical user interface from which the operator chooses a region of the body of interest, and which follows a workflow described with reference to FIGS. 17, 19, 21 and 23, is depicted in FIG. 17. The operator can, for example, choose a region of interest by highlighting, for example, using a touch screen or a mouse controlled cursor, a region of interest on an illustration of the body set forth on the user interface or can choose a region of interest from a menu such as a pull down menu. Hierarchical groupings of regions of interest can be provided. FIG. 18 depicts another embodiment of a graphical user interface from which an operator can choose a region of interest, and an alternative work flow is described herein with reference to FIGS. 18, 20, 22 and 24.

Upon choosing the region of the body to be imaged, the operator may be prompted to select from among different available baseline protocols, each of which may have preset parameters associated therewith. For example, FIG. 17 illustrates a user interface presenting a single protocol option, labeled as "Head Protocol 1," which, upon selection, can display a default flow rate and volume for each phase, along with the total diagnostic contrast volume and total diagnostic saline volume, as also shown in FIG. 17. FIG. 18 illustrates a user interface presenting multiple baseline protocols from among which the baseline protocol can be selected. The selected baseline protocol may have additional parameters associated therewith, such as injection pressure or flow rate limits, iodine concentration, scan duration, whether a test bolus is performed, etc., which may or may not be displayed and which may or may not be capable of being adjusted. FIG. 18 represents an example where additional details about the particular baseline protocol selected are displayed to the operator. An indicator may also be associated with the preset protocol indicating that the particular protocol can be adjusted based on a tube voltage modification rule, such as through the use of tube voltage modification factors as discussed above. The exemplary interfaces of FIG. 17 and FIG. 18 represent this by the "$kV_p$" icon associated with the "Head Protocol 1" and the "Cardiac w/Bolus Tracking" protocols. Other available protocols may not have a tube voltage modification option associated therewith, such as the "Dr A's Cardiac" protocol in FIG. 18.

Following selection of the region to be imaged and the baseline protocol, the operator can be prompted to enter values for the tube voltage that will be used. FIG. 19 depicts an example of a graphical interface wherein the "Tube Voltage" can be selected or entered. In this example, the tube voltage can be selected from among several preset values, though the tube voltage can also be entered using a keypad or the like. The tube voltage value may also be automatically populated based on the capabilities or setting of the associated scanner. FIG. 20 depicts another example of an interface wherein "Tube Voltage" can be selected from among various choices. In the embodiment of FIG. 20, "Patient Weight" and "Concentration" are additional parameters available for selection by the operator. The particular parameters depicted in FIGS. 19 and 20 are not intended to be limiting, and other parameters are contemplated for selection by the operator consistent with the discussion above.

Following selection of the tube voltage, baseline protocol and/or other inputs such as patient weight and iodine concentration, the implementation software of the parameter generator can determine the appropriate modification of the baseline protocol, such as through the determination of a tube voltage modification factor. The operator can then be presented with an interface informing the operator of the parameters selected and the associated adjustment made as a result of the selected tube voltage value. An example of one such interface is shown in FIG. 21, which confirms to the operator that the tube voltage value of 100 kV$_p$ has been selected and, under "Notice," that the selected tube voltage value is associated with a 19% decrease in the volume of contrast from the baseline contrast volume. FIG. 22 similarly depicts an example of an interface which informs the operator of the selected patient weight, iodine concentration, and tube voltage values and that a 19% decrease in contrast volume is associated with the particular tube voltage selected from the baseline value.

Figure 23:
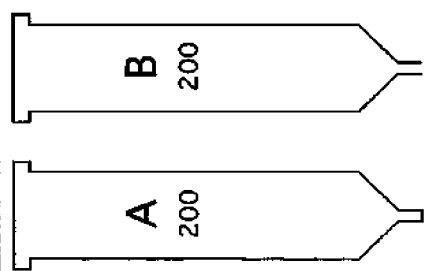
FIG. 23 illustrates an embodiment of a graphical interface which presents an operator with a computed injection protocol.
Figure 24:
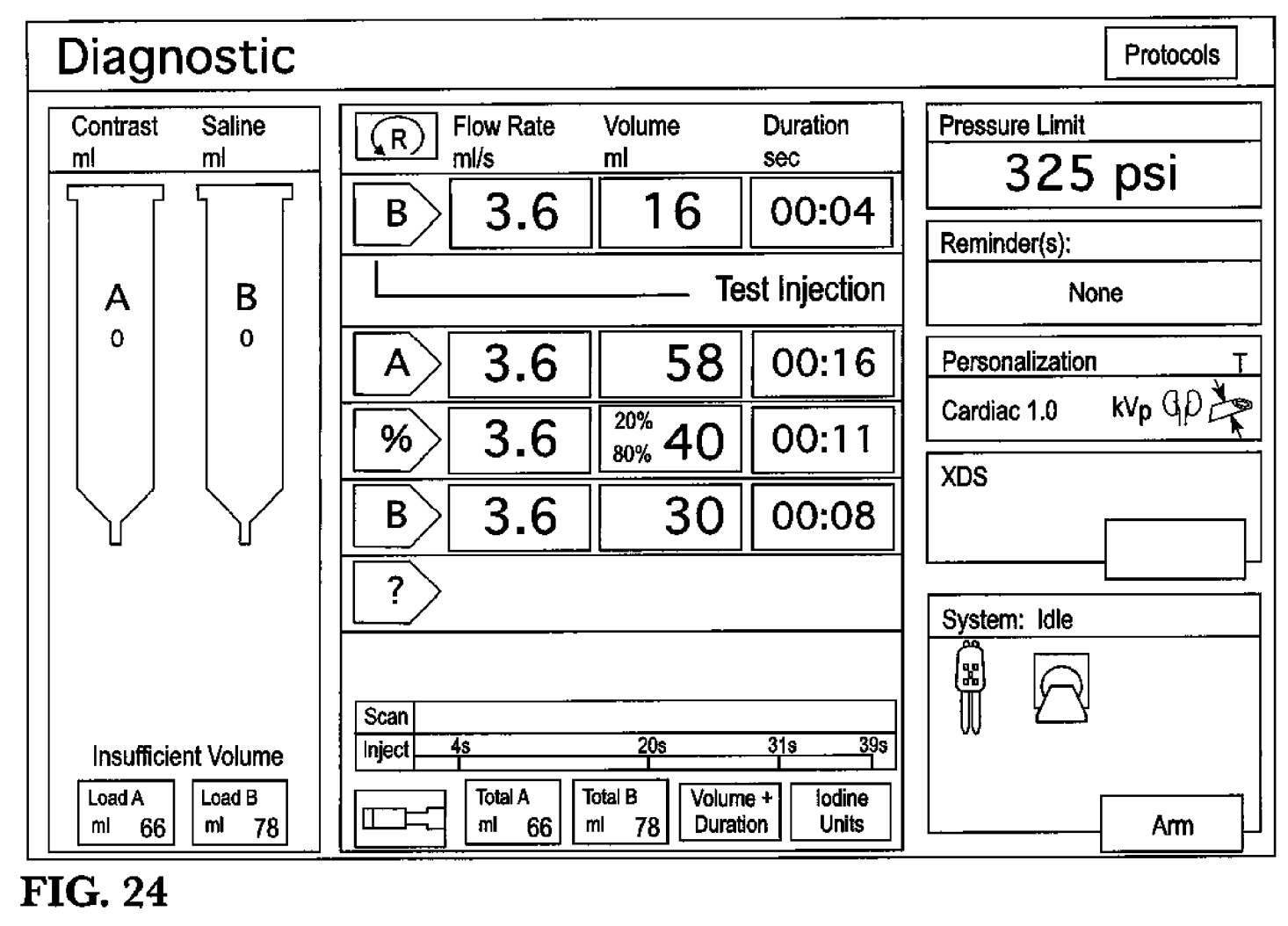

Based upon the selection of tube voltage made, the implementation software computes an injection protocol using the tube voltage modification factor. The protocol parameters such as the flow rates and volumes for the phases (including the test injection, if any), can then be presented to the operator for his or her review. One such example of an interface displaying a computed injection protocol is shown in FIG. 23. Another such example is depicted in FIG. 24.

Once review of the computed protocols is complete, the operator can initiate the injection process, which will be performed according to the particulars of the generated protocol.

Figure 25:
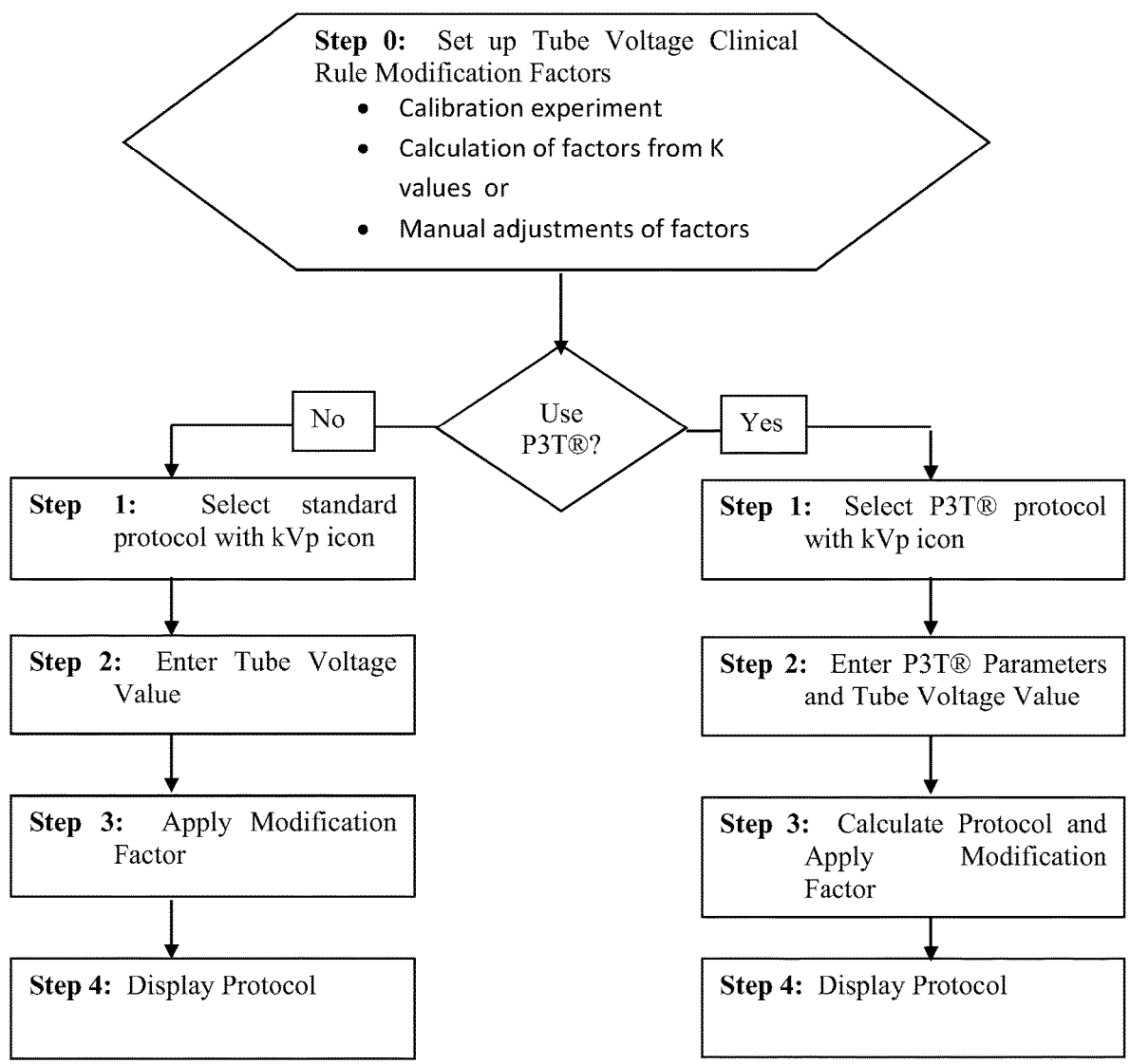
FIGS. 25-27 illustrate examples of the methodology exemplified in various embodiments of the present invention.

FIG. 25 depicts one example of the methodology associated with the embodiments involving tube voltage modification. The left hand side of the chart illustrates an example of this methodology applied to a standard protocol. Step 1 represents selection by the operator of a standard protocol, consistent with FIG. 17. Step 2 represents selection of the tube voltage from the list of tube voltages illustrated in FIG. 19. Step 3 depicts application of the modification factor to the parameters in accordance with the particular tube voltage selected in step 2. This step corresponds to that illustrated in connection with the graphical user interface of FIG. 21. Step 4 represents the display of the modified protocol, as shown in FIG. 23. Similarly, steps 1-4 on the right hand side of the chart depict application of the tube voltage modification to a preset protocol of the type that can be obtained using one or more of the P3T® Technology products available from MEDRAD, INC., a business of Bayer HealthCare. These steps follow the illustrations of FIGS. 18, 20, 22 and 24, respectively.

Figure 26:
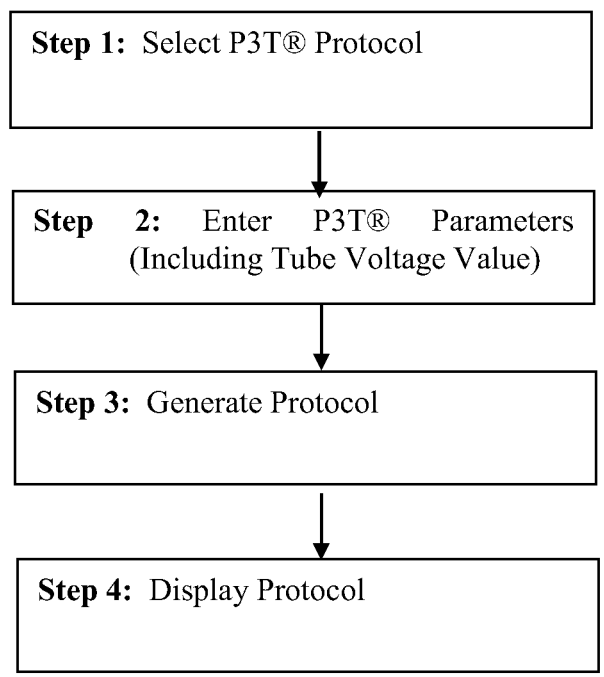

FIG. 26 depicts an example of the methodology underlying the embodiments in which the tube voltage parameter is integrated directly into the algorithm(s) of the present invention. Step 2 illustrates entry of the parameters, such as the appropriate tube voltage value, into the algorithms embodied in, for example, the P3T® Cardiac or P3T® PA products, for imaging of the vasculature of the heart and lungs, respectively. Embodying the adjusted dosing factors obtained from this method, the resulting protocol is generated in step 3 and then displayed in step 4.

Figure 27:
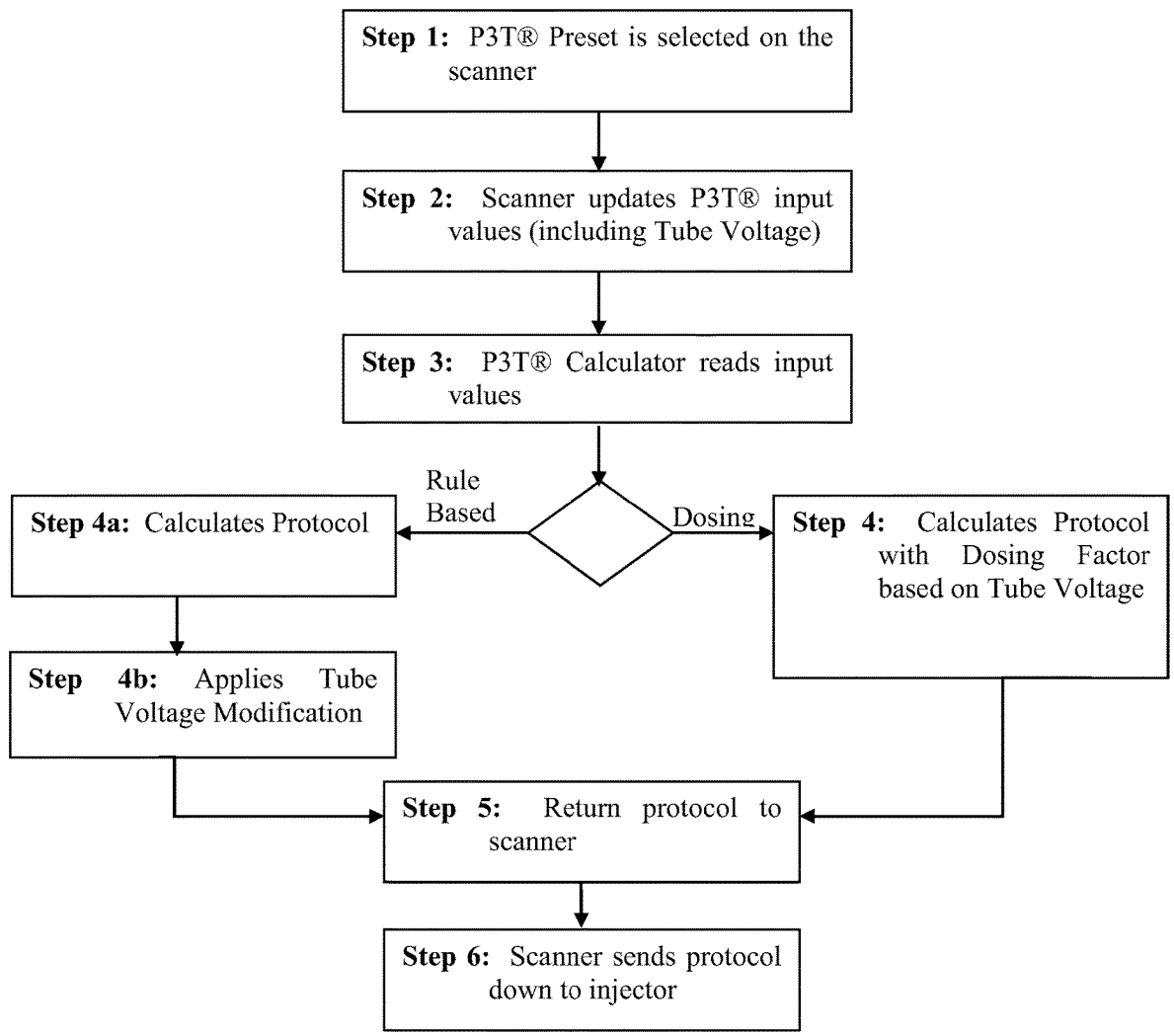

FIG. 27 illustrates an example of the methodology underlying the embodiments in which the protocol calculations are performed with at least some inputs obtained from the scanner. Step 1 shows that the initial protocol may be selected from the scanner, with the scanner updating in step 2 the entered input values inclusive of tube voltage. After the input values are read in step 3, the protocol calculator then determines the resulting protocol either by employing the rule-based modifications represented by steps 4a and 4b on the left hand side of the chart or the dosing factors represented by step 4 on the right hand side. Steps 5 and 6 represent the actions of conveying the resulting protocol to the scanner (e.g., for display) and also conveying it back to the injector, respectively.

The representative embodiments set forth above are discussed primarily in the context of CT imaging. However, the devices, systems and methods described herein have wide applicability to the injection of pharmaceuticals. For example, the systems, devices and methods discussed above may be useful in connection with the injection of contrast media for tomographic imaging procedures other than CT.

In general, the embodiments of a parameter generation system described above determine the parameters of an initial protocol using information available to the operator, including information about the tube voltage to be applied during the imaging procedure. The initial protocol provides information on the volume of one or more fluids to be delivered to, for example, enable preloading of one or more syringes. The parameters of the generated protocol may be adjusted on the basis of characterization of the cardiovascular system. The parameter generation systems of this disclosure were described in connection with an injection including an initial contrast only injection phase and a subsequent admixture phase. As will be understood by one skilled in the art, the present parameter generation system is applicable to the injection of various pharmaceuticals, with or without injection of diluent of flushing fluids, via injection protocols that can include one, two of more phases.

Although the present invention has been described in detail in connection with the above embodiments and/or examples, it should be understood that such detail is illustrative and not restrictive, and that those skilled in the art can make variations without departing from the invention. The scope of the invention is indicated by the following claims rather than by the foregoing description. All changes and variations that come within the meaning and range of equivalency of the claims are to be embraced within their scope.

The invention claimed is:
1. A patient imaging system, comprising an imaging system and a parameter generator of the patient imaging system to determine parameters of at least a first phase of an injection procedure, wherein the imaging system comprises a scanner comprising at least one x-ray tube and wherein the parameter generator comprises a processor and is programmed to determine at least one of the parameters on the basis of a voltage to be applied to the at least one x-ray tube during an imaging procedure,
    wherein the parameter generator is programmed to determine at least one of a volume of a pharmaceutical fluid to be injected during at least the first phase and a flow rate of the pharmaceutical fluid to be injected during at least the first phase on the basis of the voltage to be applied to the at least one x-ray tube during the imaging procedure,
    wherein the parameter generator is programmed to determine the volume of the pharmaceutical fluid to be injected during at least the first phase by adjusting a volume parameter of a baseline injection protocol, and
    wherein the patient imaging system further comprises an injector system in operable communication with the parameter generator, and comprising at least one source of the pharmaceutical fluid, wherein the injector system injects the pharmaceutical fluid during at least the first phase according to the determination of the volume of the pharmaceutical fluid to be injected during at least the first phase.

2. The patient imaging system of claim 1, wherein data representing the baseline injection protocol exists in a memory of the patient imaging system or accessible to the patient imaging system.

3. The patient imaging system of claim 1, wherein the parameter generator is programmed to determine the baseline injection protocol on the basis of one or more criteria inputted by an operator.

4. The patient imaging system of claim 1, wherein the parameter generator is programmed to determine the volume of the pharmaceutical fluid to be injected during at least the first phase by applying a tube voltage modification factor to the volume parameter of the baseline injection protocol.

5. The patient imaging system of claim 1, wherein the parameter generator is programmed to determine the flow rate of the pharmaceutical fluid to be injected during at least the first phase by adjusting a flow rate parameter of a baseline injection protocol.

6. The patient imaging system of claim 5, wherein data representing the baseline injection protocol exists in a memory of the patient imaging system or accessible to the patient imaging system.

7. The patient imaging system of claim 5, wherein the parameter generator is programmed to determine the baseline injection protocol on the basis of one or more criteria inputted by an operator.

8. The patient imaging system of claim 5, wherein the parameter generator is programmed to determine the flow rate of the pharmaceutical fluid to be injected during at least the first phase by dividing the volume of the pharmaceutical fluid to be injected during the first phase by an injection duration of the first phase.

9. A method of operating a system for controlling an injector system for delivering a pharmaceutical fluid to a patient as part of an imaging procedure, the injector system in operative connection with an imaging system comprising a scanner comprising at least one x-ray tube, the steps of the method comprising:
  (a) determining, by a parameter generator of the system, wherein the parameter generator comprises a processor, injection parameters of at least a first phase of an injection procedure, wherein at least one of the injection parameters is determined on the basis of a voltage to be applied to the at least one x-ray tube during the imaging procedure;
  (b) controlling, by the system, the injector system at least in part on the basis of the determined injection parameters,
  wherein the parameter generator determines at least one of a volume of a pharmaceutical fluid to be injected during at least the first phase and a flow rate of the pharmaceutical fluid to be injected during at least the first phase on the basis of the voltage to be applied to the at least one x-ray tube during the imaging procedure, and
  wherein the parameter generator determines the volume of the pharmaceutical fluid to be injected during at least the first phase by adjusting a volume parameter of a baseline injection protocol; and
  (c) injecting, by the injector system, the pharmaceutical fluid during at least the first phase according to the determination of the volume of the pharmaceutical fluid to be injected during at least the first phase.

10. The method of claim 9, wherein data representing the baseline injection protocol is recalled from a memory associated with or accessible by at least one of the injector system, the imaging system, and the parameter generator.

11. The method of claim 9, wherein the baseline injection protocol is determined on the basis of one or more criteria inputted by an operator.

12. The method of claim 9, wherein the volume of the pharmaceutical fluid to be injected during at least the first phase of the injection procedure is determined by applying a tube voltage modification factor to the volume parameter of the baseline injection protocol.

13. The method of claim 9, wherein the flow rate of the pharmaceutical fluid to be injected during at least the first phase is determined by adjusting a flow rate parameter of the baseline injection protocol.

14. The method of claim 13, wherein data representing the baseline injection protocol is recalled from a memory associated with or accessible by at least one of the injector system, the imaging system, and the parameter generator.

15. The method of claim 13, wherein the baseline injection protocol is determined on the basis of one or more criteria inputted by an operator.

16. The method of claim 13, wherein the flow rate of the pharmaceutical fluid to be injected during at least the first phase is determined by dividing the volume of the pharmaceutical fluid to be injected during the first phase by an injection duration of the first phase.

17. The method of claim 9, the method further comprising the step of populating the determined injection parameters on a graphical user interface associated with at least one of the injector system and the imaging system.

18. A method of generating an injection protocol for use with an injector system in operative connection with an imaging system comprising a scanner comprising at least one x-ray tube, the method comprising the steps of:
  (a) determining, by a parameter generator comprising a processor, injection parameters of at least a first phase of an injection procedure, wherein at least one of the injection parameters is determined on the basis of a voltage to be applied to the at least one x-ray tube during an imaging procedure,
  wherein the parameter generator determines at least one of a volume of a pharmaceutical fluid to be injected during at least the first phase and a flow rate of the pharmaceutical fluid to be injected during at least the first phase on the basis of the voltage to be applied to the at least one x-ray tube during the imaging procedure, and
  wherein the parameter generator determines the volume of the pharmaceutical fluid to be injected during at least the first phase by adjusting a volume parameter of a baseline injection protocol; and
  (b) injecting, by the injector system, the pharmaceutical fluid during at least the first phase according to the determination of the volume of the pharmaceutical fluid to be injected during at least the first phase.

19. The method of claim 18, the method further comprising the step of receiving, at the parameter generator, information identifying a region of the body to be scanned, wherein at least one of the injection parameters is determined on the basis of the region of the body to be scanned.

20. The method of claim 18, further comprising the step of receiving, at the parameter generator, information about the weight of a patient, wherein at least one of the injection parameters is determined on the basis of the weight of the patient.

21. An injection system for delivering a pharmaceutical fluid to a patient via an injection procedure performed in connection with an imaging procedure, the imaging procedure being performed with an imaging system comprising a scanner having at least one x-ray tube, the injection system comprising:

- a parameter generator comprising a processor, wherein the parameter generator is programmed for determining parameters of at least a first phase of the injection procedure wherein at least one of the parameters is determined on the basis of a voltage to be applied to the at least one x-ray tube of the imaging system during the imaging procedure,
- wherein the parameter generator is programmed to determine at least one of a volume of the pharmaceutical fluid to be injected during at least the first phase and a flow rate of the pharmaceutical fluid to be injected during at least the first phase on the basis of the voltage to be applied to the at least one x-ray tube during the imaging procedure, and
- wherein the parameter generator is programmed to determine the volume of the pharmaceutical fluid to be injected during at least the first phase by adjusting a volume parameter of a baseline injection protocol,
- such that the injection system delivers the pharmaceutical fluid to the patient during at least the first phase of the injection procedure according to the determination of the volume of the pharmaceutical fluid to be injected during at least the first phase.

22. The injection system of claim 21, wherein data representing the baseline injection protocol exists in a memory of the injection system or accessible to the injection system.

23. The injection system of claim 21, wherein the parameter generator is programmed to determine the baseline injection protocol on the basis of one or more criteria inputted by an operator.

24. The injection system of claim 21, wherein the parameter generator is programmed to determine the volume of the pharmaceutical fluid to be injected during at least the first phase by applying a tube voltage modification factor to the volume parameter of the baseline injection protocol.

25. The injection system of claim 21, wherein the parameter generator is programmed to determine the flow rate of the pharmaceutical fluid to be injected during at least the first phase by adjusting a flow rate parameter of a baseline injection protocol.

26. The injection system of claim 25, wherein data representing the baseline injection protocol exists in a memory of the injection system or accessible to the injection system.

27. The injection system of claim 25, wherein the parameter generator is programmed to determine the baseline injection protocol on the basis of one or more criteria inputted by an operator.

28. The injection system of claim 25, wherein the parameter generator is programmed to determine the flow rate of the pharmaceutical fluid to be injected during at least the first phase by dividing the volume of the pharmaceutical fluid to be injected during the first phase by an injection duration of the first phase.

* * * * *